United States Patent
Agrawal et al.

(10) Patent No.: US 10,639,510 B2
(45) Date of Patent: May 5, 2020

(54) HUMAN MUSCULOSKELETAL SUPPORT AND TRAINING SYSTEM METHODS AND DEVICES

(71) Applicant: The Trustees of Columbia University in the City of New York, New York, NY (US)

(72) Inventors: Sunil K. Agrawal, Newark, DE (US); Moiz Khan, Sayreville, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/913,808

(22) Filed: Mar. 6, 2018

(65) Prior Publication Data
US 2018/0264306 A1 Sep. 20, 2018

Related U.S. Application Data

(60) Provisional application No. 62/473,986, filed on Mar. 20, 2017.

(51) Int. Cl.
*A63B 21/00* (2006.01)
*A63B 26/00* (2006.01)
(Continued)

(52) U.S. Cl.
CPC .......... *A63B 21/00181* (2013.01); *A61F 5/02* (2013.01); *A61H 1/001* (2013.01);
(Continued)

(58) Field of Classification Search
CPC .......... A63B 21/00181; A63B 24/0075; A63B 24/0006; A63B 24/0062; A63B 21/0058; A63B 21/151; A63B 21/4009; A63B 21/00178; A63B 24/0087; A63B 26/003; A63B 2220/805; A63B 2220/51; A63B 2220/40; A63B 2220/05;
(Continued)

(56) References Cited

U.S. PATENT DOCUMENTS

| 5,020,790 A | 6/1991 | Beard et al. |
| 5,509,894 A | 4/1996 | Mason et al. |

(Continued)

FOREIGN PATENT DOCUMENTS

| CN | 102579229 B | 11/2013 |
| EP | 1716834 A2 | 11/2006 |

(Continued)

OTHER PUBLICATIONS

Adamovich et al., "Sensorimotor training in virtual reality: A review", NeuroRehabilitation, vol. 25, No. 1, pp. 29-44, 2009.
(Continued)

*Primary Examiner* — Sundhara M Ganesan
(74) *Attorney, Agent, or Firm* — Potomac Law Group, PLLC; Mark A. Catan

(57) ABSTRACT

A Trunk Support Trainer (TruST) is a dynamic device that trains subjects to improve strength and coordination of the upper body, while seated, and facilitates the trunk to safely move beyond the region of stability. In embodiments, the device creates an 'assist-as-needed' force field to support postures beyond stable sitting positions.

28 Claims, 20 Drawing Sheets

(51) Int. Cl.
*A63B 24/00* (2006.01)
*A63B 21/005* (2006.01)
*A61F 5/02* (2006.01)
*G06F 3/01* (2006.01)
*A61H 1/00* (2006.01)

(52) U.S. Cl.
CPC .... *A63B 21/0058* (2013.01); *A63B 21/00178* (2013.01); *A63B 21/151* (2013.01); *A63B 21/4009* (2015.10); *A63B 24/0006* (2013.01); *A63B 24/0062* (2013.01); *A63B 24/0075* (2013.01); *A63B 24/0087* (2013.01); *A63B 26/003* (2013.01); *G06F 3/011* (2013.01); *A61H 2201/14* (2013.01); *A61H 2201/1652* (2013.01); *A61H 2201/5007* (2013.01); *A61H 2201/5061* (2013.01); *A61H 2201/5084* (2013.01); *A61H 2201/5092* (2013.01); *A61H 2203/0431* (2013.01); *A61H 2230/625* (2013.01); *A63B 2024/0096* (2013.01); *A63B 2220/05* (2013.01); *A63B 2220/40* (2013.01); *A63B 2220/51* (2013.01); *A63B 2220/805* (2013.01); *A63B 2220/806* (2013.01)

(58) Field of Classification Search
CPC ...... A63B 2024/0096; A63B 2220/806; A61H 1/001; A61H 2201/5007; A61H 2201/1652; A61H 2201/14; A61H 2203/0431; A61H 2201/5061; A61H 2201/5092; A61H 2201/5084; A61H 2230/625; G06F 3/011; A61F 5/02
See application file for complete search history.

(56) References Cited

U.S. PATENT DOCUMENTS

| | | | |
|---|---|---|---|
| 5,961,541 A | 10/1999 | Ferrati | |
| 5,961,544 A | 10/1999 | Goldman et al. | |
| 6,666,831 B1 | 12/2003 | Edgerton et al. | |
| 6,689,075 B2 | 2/2004 | West | |
| 7,125,388 B1 | 10/2006 | Reinkensmeyer et al. | |
| 7,150,722 B1 | 12/2006 | Tyrrell | |
| 7,462,138 B2 | 12/2008 | Shetty et al. | |
| 7,544,155 B2 | 6/2009 | Agrawal et al. | |
| 7,549,969 B2 | 6/2009 | van den Bogert | |
| 7,878,993 B2 | 2/2011 | Agrawal et al. | |
| 8,147,436 B2 | 4/2012 | Agrawal et al. | |
| 8,608,479 B2 | 12/2013 | Liu | |
| 8,613,691 B2 | 12/2013 | Bosecker et al. | |
| 8,684,890 B2 | 4/2014 | Bosecker et al. | |
| 8,915,871 B2 * | 12/2014 | Einav | A61B 5/1116 601/5 |
| 9,532,916 B2 | 1/2017 | Tsui et al. | |
| 9,604,369 B2 | 3/2017 | Angold et al. | |
| 9,868,012 B2 * | 1/2018 | Burdea | A63B 21/06 |
| 2002/0023986 A1 * | 2/2002 | Nicholson | G06F 3/011 248/118 |
| 2003/0181299 A1 * | 9/2003 | Matjacic | A61B 5/1036 482/146 |
| 2005/0043661 A1 | 2/2005 | Nashner | |
| 2005/0101448 A1 | 5/2005 | He et al. | |
| 2005/0239613 A1 | 10/2005 | Colombo et al. | |
| 2007/0275830 A1 | 11/2007 | Lee et al. | |
| 2007/0282228 A1 * | 12/2007 | Einav | A63B 21/4021 601/33 |
| 2008/0009771 A1 | 1/2008 | Perry et al. | |
| 2008/0132383 A1 * | 6/2008 | Einav | A61H 1/02 482/8 |
| 2008/0242521 A1 * | 10/2008 | Einav | A61B 5/1116 482/110 |
| 2009/0111670 A1 * | 4/2009 | Williams | A63B 23/0464 482/146 |
| 2009/0312165 A1 * | 12/2009 | Rempe | A63B 22/18 482/146 |
| 2010/0306715 A1 * | 12/2010 | Geisner | G06F 3/017 715/863 |
| 2011/0251533 A1 | 10/2011 | Han et al. | |
| 2011/0256983 A1 * | 10/2011 | Malack | A61H 1/0266 482/4 |
| 2011/0312473 A1 * | 12/2011 | Chu | A63B 22/0235 482/54 |
| 2012/0004581 A1 | 1/2012 | Dinon | |
| 2012/0094814 A1 * | 4/2012 | Atkins | A61B 5/486 482/142 |
| 2012/0190505 A1 * | 7/2012 | Shavit | A63B 71/0622 482/8 |
| 2012/0197168 A1 | 8/2012 | Agrawal et al. | |
| 2012/0253247 A1 * | 10/2012 | Aoki | A61H 3/00 601/112 |
| 2013/0158444 A1 | 6/2013 | Herr et al. | |
| 2013/0203571 A1 * | 8/2013 | Kwon | A61H 1/0237 482/145 |
| 2013/0237378 A1 * | 9/2013 | Carrell | A63C 17/061 482/51 |
| 2014/0094345 A1 | 4/2014 | Kim et al. | |
| 2014/0190289 A1 | 7/2014 | Zhu | |
| 2015/0061992 A1 * | 3/2015 | Lamberty | G06F 3/017 345/156 |
| 2015/0238382 A1 | 8/2015 | Park et al. | |
| 2015/0258431 A1 * | 9/2015 | Stafford | A63F 13/213 463/31 |
| 2015/0297934 A1 | 10/2015 | Agrawal et al. | |
| 2015/0316985 A1 * | 11/2015 | Levesque | G06T 19/006 345/156 |
| 2016/0030833 A1 * | 2/2016 | Klassen | H04W 4/029 434/247 |
| 2016/0077547 A1 * | 3/2016 | Aimone | G06F 3/012 345/8 |
| 2016/0179199 A1 * | 6/2016 | Levesque | G06F 3/011 340/407.2 |
| 2016/0217614 A1 * | 7/2016 | Kraver | G06T 19/006 |
| 2016/0250094 A1 | 9/2016 | Amundson et al. | |
| 2016/0302989 A1 * | 10/2016 | Loduca | A61H 1/0237 |
| 2016/0313822 A1 * | 10/2016 | Krishnakumar | G06F 1/1632 |
| 2016/0346156 A1 * | 12/2016 | Walsh | A63B 21/4009 |
| 2016/0349835 A1 * | 12/2016 | Shapira | G06F 3/011 |
| 2017/0027803 A1 * | 2/2017 | Agrawal | A61B 5/6828 |
| 2017/0042717 A1 | 2/2017 | Agrawal et al. | |
| 2017/0278304 A1 * | 9/2017 | Hildreth | G02B 27/0172 |
| 2017/0309071 A1 * | 10/2017 | Benko | G06F 3/011 |
| 2017/0352188 A1 * | 12/2017 | Levitt | G06F 1/1626 |
| 2018/0005438 A1 * | 1/2018 | Mathey-Owens | G02B 27/0172 |
| 2018/0005443 A1 * | 1/2018 | Poulos | G06F 3/017 |
| 2018/0046245 A1 * | 2/2018 | Schwarz | G02B 27/0093 |
| 2018/0067545 A1 * | 3/2018 | Provancher | G06F 3/011 |
| 2018/0110670 A1 * | 4/2018 | Saglia | A63B 69/0057 |
| 2018/0143756 A1 * | 5/2018 | Mildrew | G06F 3/011 |
| 2018/0158250 A1 * | 6/2018 | Yamamoto | G06T 19/20 |
| 2018/0232050 A1 * | 8/2018 | Ofek | G06F 3/016 |
| 2018/0349690 A1 * | 12/2018 | Rhee | G06T 7/13 |
| 2018/0356636 A1 * | 12/2018 | Kimura | G02B 27/0179 |
| 2019/0057550 A1 * | 2/2019 | Aurongzeb | G06T 19/006 |

FOREIGN PATENT DOCUMENTS

| | | |
|---|---|---|
| KR | 20110041154 A | 4/2011 |
| WO | 2008096210 A1 | 8/2008 |
| WO | 2012024562 A2 | 2/2012 |
| WO | 2013049658 A1 | 4/2013 |
| WO | 2015120186 A1 | 8/2015 |

OTHER PUBLICATIONS

Aoyagi et al., "An assistive robotic device that can synchronize to the pelvic motion during human gait training", Rehabilitation Robotics, 2005. ICORR 2005. 9th International Conference on Jun. 28, 2005, pp. 565-568.

(56) References Cited

OTHER PUBLICATIONS

Banala et al., "Robot assisted gait training with active leg exoskeleton (ALEX)", 2nd IEEE RAS & EMBS International Conference on Biomedical Robotics and Biomechatronics, Oct. 19, 2008, pp. 653-658 (Abstract).
Banala et al., "Robot assisted gait training with active leg exoskeleton (ALEX)", IEEE Transactions on Neural Systems and Rehabilitation Engineering, Feb. 1, 2009, vol. 17(1), pp. 2-8 (Abstract).
Bastian, "Understanding sensorimotor adaptation and learning for rehabilitation", Dec. 1, 2008, vol. 21(6), pp. 628-633.
Borggraefe et al., "Improved gait parameters after robotic-assisted locomotor treadmill therapy in a 6-year-old child with cerebral palsy", Movement Disorders, Jan. 30, 2008, vol. 23(2), pp. 280-283.
Cai et al., "Implications of assist-as-needed robotic step training after a complete spinal cord injury on intrinsic strategies of motor learning", Journal of Neuroscience, vol. 26/Issue 1, pp. 10564-10568, Oct. 11, 2016.
Chen et al., "The relationship between sitting stability and functional performance in patients with paraplegia", Arch. Phys. Med. Rehabil., vol. 84, No. 9, pp. 1276-1281, 2003.
European Search Report issued in the corresponding EP Application No. 15783400.3, dated Dec. 14, 2017.
Extended European Search Report for European Patent Application No. 15783400.3 dated Dec. 14, 2017.
Fallang et al., "Goal directed reaching and postural control in supine position in healthy infants", Behav. Brain Res., vol. 115, No. 1, pp. 9-18, 2000.
Forssberg et al., "Postural adjustments in sitting humans following external perturbations: muscle activity and kinematics", Exp. Brain Res., vol. 97, No. 3, pp. 515-527, 1994.
Hadders-Algra et al., "Ontogeny of postural adjustments during sitting in infancy: variation, selection and modulation.", J. Physiol., vol. 493 ( Pt 1, pp. 273-288, 1996.
Hadders-Algra, "Typical and atypical development of reaching and postural control in infancy", Dev. Med. Child Neurol., vol. 55, No. Suppl.4, pp. 5-8, 2013.
Harbourne et al., "Nonlinear analysis of the development of sitting postural control", Dev. Psychobiol., vol. 42, No. 4, pp. 368-377, 2003.
Hedberg et al., "Postural adjustments due to external perturbations during sitting in 1-month-old infants: Evidence for the innate origin of direction specificity", Exp. Brain Res., vol. 157, No. 1, pp. 10-17, 2004.
Hedberg, "Early development of postural adjustments in standing with and without support", Exp. Brain Res., vol. 178, No. 4, pp. 439-449, 2007.
International Preliminary Report on Patentability for International Application No. PCT/US2015/026941 dated Nov. 3, 2016.
International Search Report and Written Opinion for International Application No. PCT/US2015/026941 dated Sep. 23, 2015.
Kang et al, "A novel assist-as-needed control method to guide pelvic trajectory for gait rehabilitation", in Proc. 2014 IEEE Int. Conf. Rehab. Robot., 2015, pp. 630-635.
Khan et al., Enhancing Seated Stability Using Trunk Support Trainer ( TruST )*, IEEE Robot. Autom. Lett., vol. 2, No. 3, pp. 1609-1616, 2017.
Kleim et al., "Principles of Experience-Dependent Neural Plasticity: Implications for Rehabilitation After Brain Damage", J. Speech Lang.Hear. Res., Feb. 1, 2008, vol. 51, pp. S225-S239.
Latash et al., "Motor control theories and their applications", Medicina, vol. 46, No. 6, pp. 382-392, 2010.
Lee et al., "A virtual reality system for the assessment and rehabilitation of the activities of daily living.", Cyberpsychology Behav., vol. 6, No. 4, pp. 383-388, 2003.
Lu et al., "Development and Learning Control of a Human Limb With a Rehabilitation Exoskeleton", IEEE transactions on industrial electronics, Jul. 1 ,2014, vol. 61(7), pp. 3776-3785 (Abstract).
Maciejasz et al., "A survey on robotic devices for upper limb rehabilitation", Journal of NeuroEnigneering and Rehabilitation, vol. 11, Issue 3, Jan. 9, 2014.

Mao et al., "Human movement training with a cable driven ARm EXoskeleton (CAREX)", IEEE Trans. Neural Syst. Rehabil. Eng., vol. 23, No. 1, pp. 84-92, Jan. 2015.
Mao, "Transition from mechanical arm to human arm with CAREX: A cable driven ARm EXoskeleton (CAREX) for neural rehabilitation", in Proc. IEEE Int. Conf. Robot. Autom., 2012, pp. 2457-2462.
Martin et al., "Throwing while looking through prisms. II. Specificity and storage of multiple gaze-throw calibrations", Aug. 1, 1996, vol. 119(4), pp. 1199-1211.
Massion, "Postural control systems in developmental perspective", Neurosci. Biobehav. Rev., vol. 22, No. 4, pp. 465-472, 1998.
Merodio et al., "Exploiting joint synergy for actuation in a lower-limb active orthosis", Industrial Robot: An International Journal, Apr. 26, 2013, vol. 40(3), pp. 224-228 (Abstract).
Michaelsen et al., "Effect of trunk restraint on the recovery of reaching movements in hemiparetic patients", Stroke, vol. 32, pp. 1875-1883, 2001.
Ojha, "An Application of Virtual Reality in Rehabilitation", IEEE Southeastcon, pp. 4-6, 1994.
Olney et al., "Mechanical energy patterns in gait of cerebral palsied children with hemiplegia", Phys Ther., Sep. 1, 1987, vol. 67(9), pp. 1348-1354.
Patton et al., "Robotics and Virtual Reality?: A Perfect Marriage for Motor Control Research and Rehabilitation", Assist. Technol., 18:2, pp. 181-195, 2006.
Peshkin et al., "KineAssist: A robotic overground gait and balance training device", InRehabilitation Robotics, ICORR 2005, 9th International Conference on Jun. 28, 2005, pp. 241-246.
Rose et al., "Virtual reality: an assistive technology in neurological rehabilitation.", Current opinion in neurology, vol. 9, No. 6. pp. 461-467, 1996.
Sanes et al., "Plasticity and primary motor cortex", Annual Review of Neuroscience, Mar. 1, 2000, vol. 23(1), pp. 393-415.
Savin et al, "Poststroke Hemiparesis Impairs the Rate but not Magnitude of Adaptation of Spatial and Temporal Locomotor Features", Neurorehabil Neural Repair, Jan. 1, 2013, vol. 27(1), pp. 24-34.
Stuart, "Integration of posture and movement: Contributions of Sherrington, Hess, and Bernstein", Hum. Movement Sci, vol. 24, Nos. 5-6, pp. 621-643, 2005.
Surdilovic et al., "STRING-MAN: a new wire robot for gait rehabilitation", Robotics and Automation, 2004. Proceedings. ICRA '04. 2004 IEEE International Conference on Apr. 26, 2004, vol. 2, pp. 2031-2036 (Abstract).
Surdilovic et al., "STRING-MAN: Wire-robot technology for safe, flexible and human-friendly gait rehabilitation", InRehabilitation Robotics, 2007, ICORR 2007, IEEE 10th International Conference on Jun. 13, 2007, pp. 446-453.
Vashista, "A novel approach to apply gait synchronized external forces on the pelvis using A-TPAD to reduce walking effort", IEEE Robot Autom. Lett., vol. 1, No. 2, pp. 1118-1124, Jul. 2016.
Thielman et al., "Rehabilitation of reaching after stroke: Task-related training versus progressive resistive exercise", Arch. Phys. Med. Rehabil., vol. 85, No. 10, pp. 1613-1618, 2004.
Vallery et al., "Multidirectional transparent support for overground gait training", InRehabilitation Robotics (ICORR), 2013 IEEE International Conference on Jun. 24, 2013, pp. 1-7.
Van Der Heide et al., "Development of postural adjustments during reaching in sitting children", Exp. Brain Res., vol. 151, No. 1, pp. 32-45, 2003.
Vashista et al., "Asymmetric adaptation in human walking using the Tethered Pelvic Assist Device (TPAD)", InRehabilitation Robotics (ICORR), 2013 IEEE International Conference on Jun. 24, 2013, pp. 1-5.
Vashista et al., "Experimental studies on the human gait using a tethered pelvic assist device (T-PAD)", InRehabilitation Robotics (ICORR), 2011 IEEE International Conference, Jun. 29, 2011, pp. 1-6.
Vashista et al., "Force adaptation in human walking with symmetrically applied downward forces on the pelvis", 34th International Conference of the IEEE, Aug. 28, 2012, pp. 3312-3315.

(56) References Cited

OTHER PUBLICATIONS

Vashista, "Active tethered pelvic assist device (A-TPAD) to study force adaptation in human walking", in Proc. 2014 IEEE Int. Conf. Robot. Autom., 2014, pp. 718-723.
Veg et al., "Walkaround: Mobile Balance Support for Therapy of Walking", Neural Systems and Rehabilitation Engineering, IEEE Transactions, Jun. 10, 2008, vol. 16(3), pp. 264-269 (Abstract).
Veneman et al., "Design and Evaluation of the LOPES Exoskeleton Robot for Interactive Gait Rehabilitation", Neural Systems and Rehabilitation Engineering, IEEE Transactions, Sep. 1, 2007, vol. 15(3), pp. 379-386.
Zanotto et al., "ALEX III: A novel robotic platform with 12 DOFs for human gait training", InRobotics and Automation (ICRA), 2013 IEEE International Conference on May 6, 2013.

\* cited by examiner

HUMAN MUSCULOSKELETAL SUPPORT AND TRAINING SYSTEM METHODS AND DEVICES

CROSS-REFERENCE TO RELATED APPLICATIONS

This application claims priority to and the benefit of U.S. Provisional Application No. 62/473,986 filed Mar. 20, 2017, the content of which is incorporated herein by reference in its entirety.

BACKGROUND

Adults and children with spinal cord injury (SCI) lose their ability to sit independently due to paralysis of the trunk and limb muscles. This is a significant functional loss as active trunk and pelvis are key for successful sitting, standing, and walking. Current physical rehabilitation provides various tools including passive management for the lack of trunk control.

In contrast to adult-onset SCI, the impact of this injury on children can be even more devastating as it affects the daily functions during the critical periods of growth and development, thereby, increasing the severity and complications across the lifespan. The occurrence of neuromuscular scoliosis is in 97% of children who have an injury before the age of 5. Regardless of severity of the injury, 63% develop a curve larger than 40 degrees, needing surgical intervention. Unique to pediatric-onset SCI, scoliosis has a tremendous impact on the quality of life of the children as well as pose huge financial burden on the family and the healthcare system. There is a need to develop new approaches to provide effective therapies in this area.

SUMMARY

A Trunk Support Trainer (TruST) is a cable-driven device that (i) trains subjects to improve strength and coordination of the upper body, while seated, and (ii) facilitates the trunk to safely move beyond the region of stability. These are accomplished by creating 'assist-as-needed' force tunnels to support postures beyond stable sitting positions and progressively decrease these force fields as subjects build proficiency. Findings indicate that this approach may be useful for training children who have compromised postural stability due to neurological or musculoskeletal disorders. The TruST may be used as an assist or training device for the upper body during seated configurations in SCI patients, with ages 2-12 years.

Figure 1:
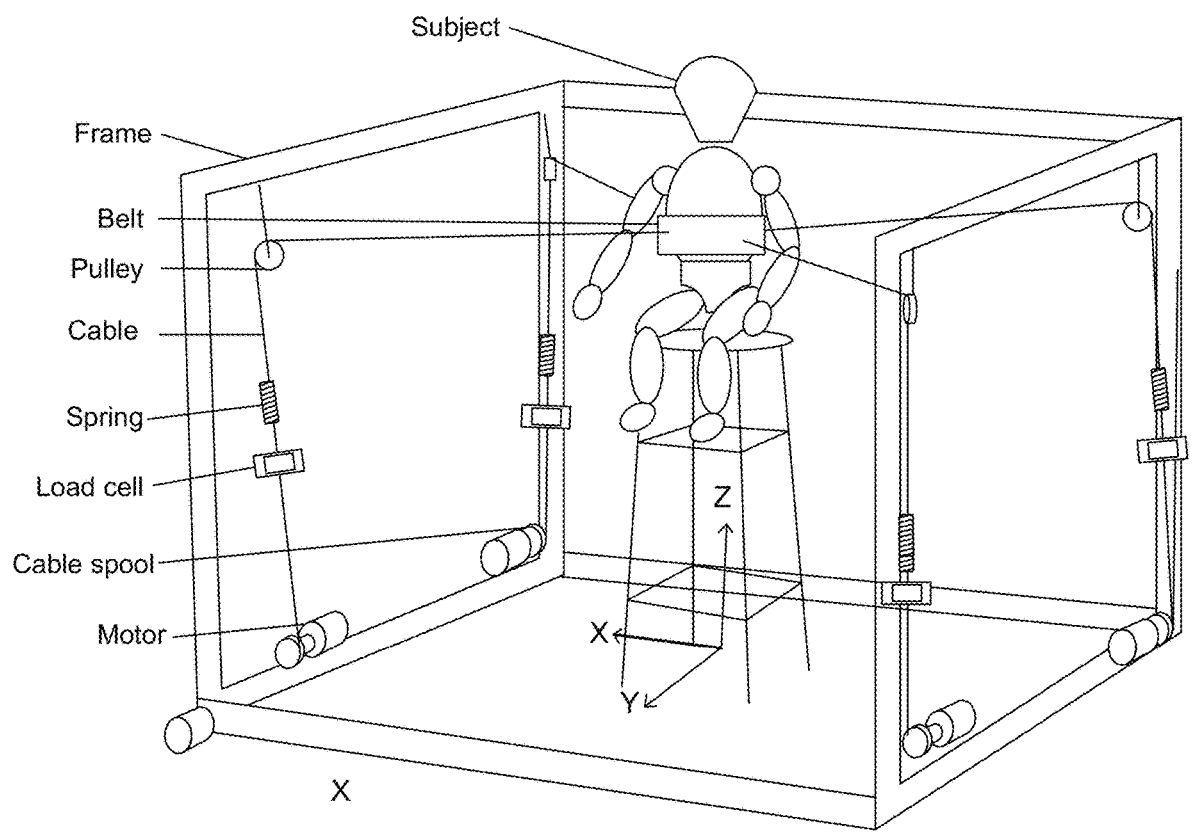
FIG. 1 shows a schematic of a posture support and detection apparatus identified herein, in embodiments, as TruST, which has four cables attached to a torso belt, along the transverse plane and four motors mounted on a stationary frame, while a spring and load cell are attached in series with each cable and a global reference frame is set at the middle of the sitting platform.

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

DETAILED DESCRIPTION

Pediatric spinal cord injury (SCI) accounts for approximately 4% of overall incidence of SCI annually. In the US, approximately 1,500 children <15 years of age experience SCI annually. In children, SCI abruptly interrupts the typical trajectory of a child's development, yet magnifying the consequences of paralysis by continued musculoskeletal growth. The current approach to rehabilitation for children with severe SCI is compensation for paralysis and adaptation to manage the consequences of SCI considered inevitable. Children are not expected to get better and parents are given little to no expectation for recovery. Equipment is prescribed to provide skeletal support and mobility, e.g., torso and leg braces, standers and wheelchairs. Despite the common practice of torso bracing to prevent scoliosis, 97% of children injured by SCI <5 years of age develop scoliosis; 63% with curve >40°. Two-thirds of these children undergo costly corrective scoliosis surgery involving repeat surgeries and hospitalizations. The trajectory of health-related quality of life across time for children with SCI indicates increased risk for pneumonia, pressure sores, urinary tract infections, kidney stones and scoliosis. Rehabilitation to improve function after pediatric-onset SCI has historically relied on interventions that 1) alter the context of performance and 2) adapt or modify the environment and/or task demands to enable performance by the individual.

A premise of the disclosed system and methods is that the spinal cord below the level of injury is plastic, smart and responds to intense skill practice and repetition. The system permits the implementation of therapies designed to 'turn-on' the nervous system below the injury via task-specific, repetitive training. The inventors have conducted a series of studies with TruST which are described herein. These include a case study of a child with CP that provides an approach to postural training disclosed herein. By extending the opportunity to practice beyond reach, defined where the body's center of mass goes outside the base of support, improved postural control was demonstrated after 6 sessions in this child. This paradigm and the TruST system provide the foundation for explorations proposed in this study.

Dynamic seated trunk control is required during the execution of many everyday tasks. These tasks require an intricate coordination between the head, upper and lower trunk, and the pelvis. Furthermore, reaching beyond the arm's length requires precise joint control and intersegmental coordination. By providing seated reach training that challenges postural control beyond the stability limits could improve postural control and expand the boundary of reach.

TruST shown in the FIG. 1 is a cable driven robotic system that facilitates postural training by controlling the applied force/moment on a region of the human trunk. Note that the functionality of this system can be embodied in other mechanical forms such as a wearable brace such as described in US20170042717 which employs a segmented body brace with linkages that can be controlled to generate torques on the upper body as described therein. The reference, US20170042717 is hereby incorporated by reference as if fully set forth in its entirety herein.

Figure 2:
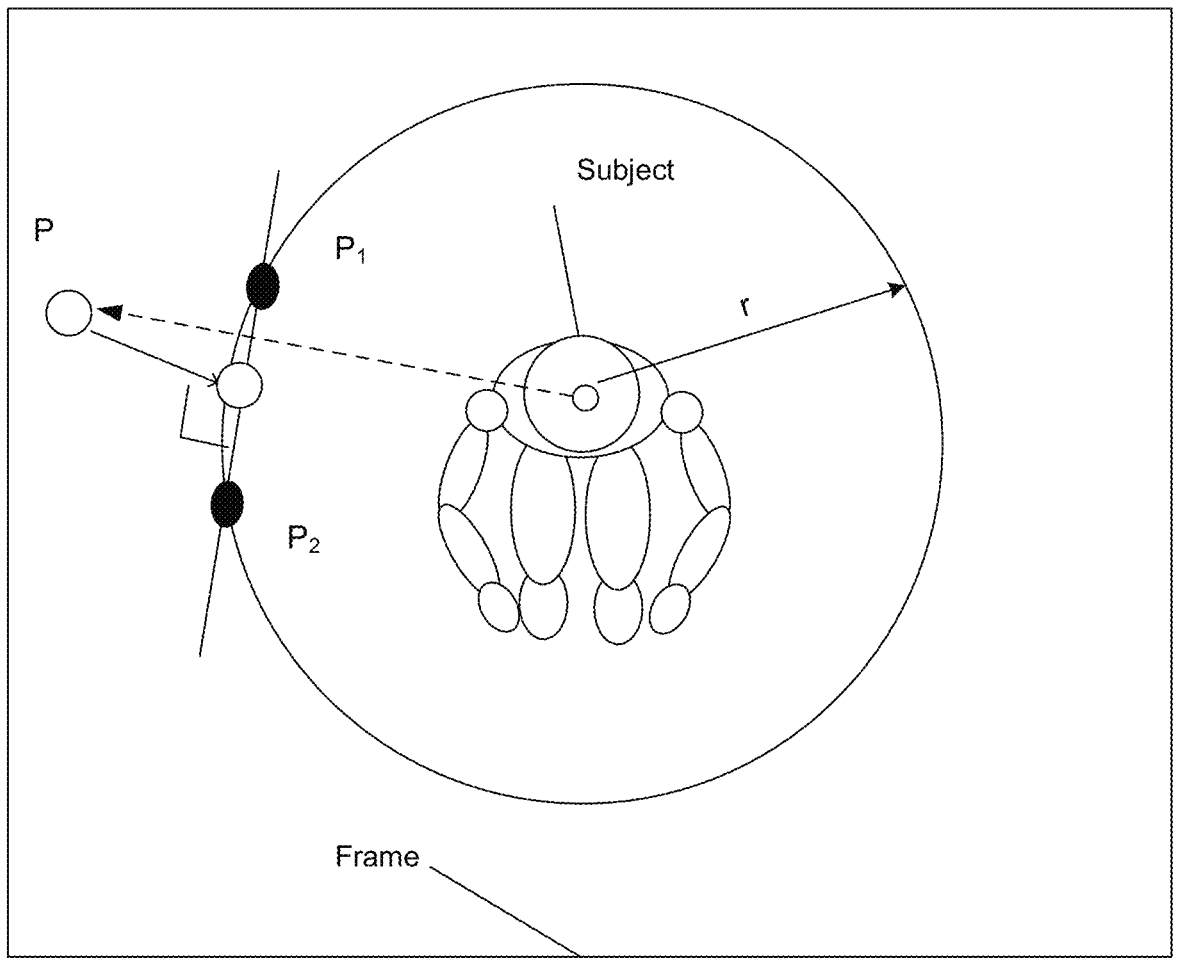
FIG. 2 shows how the high-level controller assesses the spatial position of the estimated center of the trunk P such that once P is outside a specified radius (r), a normal force is applied to assist the subject back into the force tunnel and the large circle denotes the force tunnel, determined by the boundary of stability.

FIG. 2 shows how the high-level controller assesses the spatial position of the estimated center of the trunk P such that once P is outside a specified radius (r), a normal force is applied to assist the subject back into the force tunnel and the large circle denotes the force tunnel, determined by the boundary of stability.

A force tunnel is created using an assist-as-needed force strategy, to support postures beyond the sitting stability region (See Figure immediately below), similar to the system described in US patent publication US20150297934, hereby incorporated by reference as if fully set forth in its entirety herein.

TruST utilizes four cables attached to each corner of a torso belt, while the other end of the cables are connected to servo motors attached to a fixed frame. The cable attachment points on the belt are reinforced with thermoplastic to eliminate belt deformation during force application. A tension sensor is attached in series to each cable. Pulleys are used to route cables from the motors to the torso. A cable spool is attached to the end of each motor shaft to prevent the cables from wrapping over themselves. A motion capture system is used to record the cable attachment points on the belt and pulleys to calculate the force directions. A two-stage control is implemented using Labview, a PXI real time controller, and data acquisition cards.

Human Experiments were performed with twenty healthy subjects (age 20-30 years, 12 males/8 females, 19 right-handed, and 1 left-handed). See FIGS. 4 and 5 which show a subject performing a nine-hole peg test and a modified functional reach test, respectively, that were performed during a human experiment.

Retro-reflective markers were placed on the subjects to record kinematics using a Vicon motion capture system. The subjects were seated on a stool at the center of the TruST. A belt was attached to the lower trunk (lumbar) region. During the BL, the pre-training tasks consisted of the functional reach test to determine the maximum lower trunk displacement and define the point of stability failure, and a pre-training nine-hole peg task without assistive forces.

During training, five blocks of two consecutive trials of the nine-hole peg task were conducted (massed practice). This was followed by PT stage in which both, functional reach and nine hole peg tasks, were re-assessed after removing the external assistance from TruST.

During the experiment, all subjects sat on a flat, wooden stool. The torso belt was firmly placed at the lower trunk. The subjects were asked not to use any foot or hand support while performing the functional reach task and the nine-hole peg task. However, they were allowed to move their body to complete all tasks to the best of their ability. All tasks started from a stable neutral position with the head and trunk centered over the pelvis, with elbows in external rotation and bent 90-degrees in the air. Subjects were instructed to perform each task as fast and accurately as possible, while maintaining postural control. During training, subjects were allowed to use a finger or the volar area of the wrist for support on the table, only if posture stability was lost during the placement of the pegs.

For the functional reach test, the subjects were asked to displace a wooden block anteriorly as far as they could in a controlled and self-paced manner. If the subject used any support or lost balance, the task was stopped and the point of stability failure was recorded. If the subject lost balance prematurely, they were allowed to repeat the task. Premature loss of balance was indicated if 1) the subject touched the table surface for support, or 2) there was premature foot-ground contact for displacing the piece of wood at further distance. The reach test was performed at BL and PT, with the shoulders flexed at 90-degrees and arm parallel to the floor.

The failure point was used to identify the boundary between postural stability and instability. This boundary specified the maximum anterior translation of the lower trunk before postural collapse. The nine-hole peg board (3×3 holes of 4 mm diameter) was then placed in front of the subject, with the furthest row being in line with the position of the wooden block at the time of stability failure. The subjects were instructed to grab a peg from their dominant side and to place it onto the board from right to left, working from the closest row to the furthest.

After inserting the nine pegs, subjects removed these in the same order. A complete cycle of inserting and removing pegs was identified as a single trial. Two consecutive trials conducted at a time were defined as a block. Five blocks were conducted, with the assist-as-needed, error based force for the experimental group at or beyond the predefined maximum lower trunk displacement (e.g. point of stability failure). Accordingly, the subjects moved independent of any assistance as long as they were inside the force tunnel but received assistance at and beyond their failure point. The assistive force was decreased by 2N (3.33%) after each block of training. The subjects were allowed as much rest time as they needed between sessions to a maximum of five minutes. The same protocol was followed for the control group but no assistive forces were provided.

The data were analyzed to assess the spatiotemporal changes in head, upper trunk, lower trunk, and pelvis translation and rotation between pre and post functional reach test. The data were analyzed using Matlab. The COM of the lower trunk was estimated using right and left belt markers. Translation of this trunk segment was measured in the anterior-posterior direction, from start of the trial (neutral position) to the point of stability failure.

Figure 6:
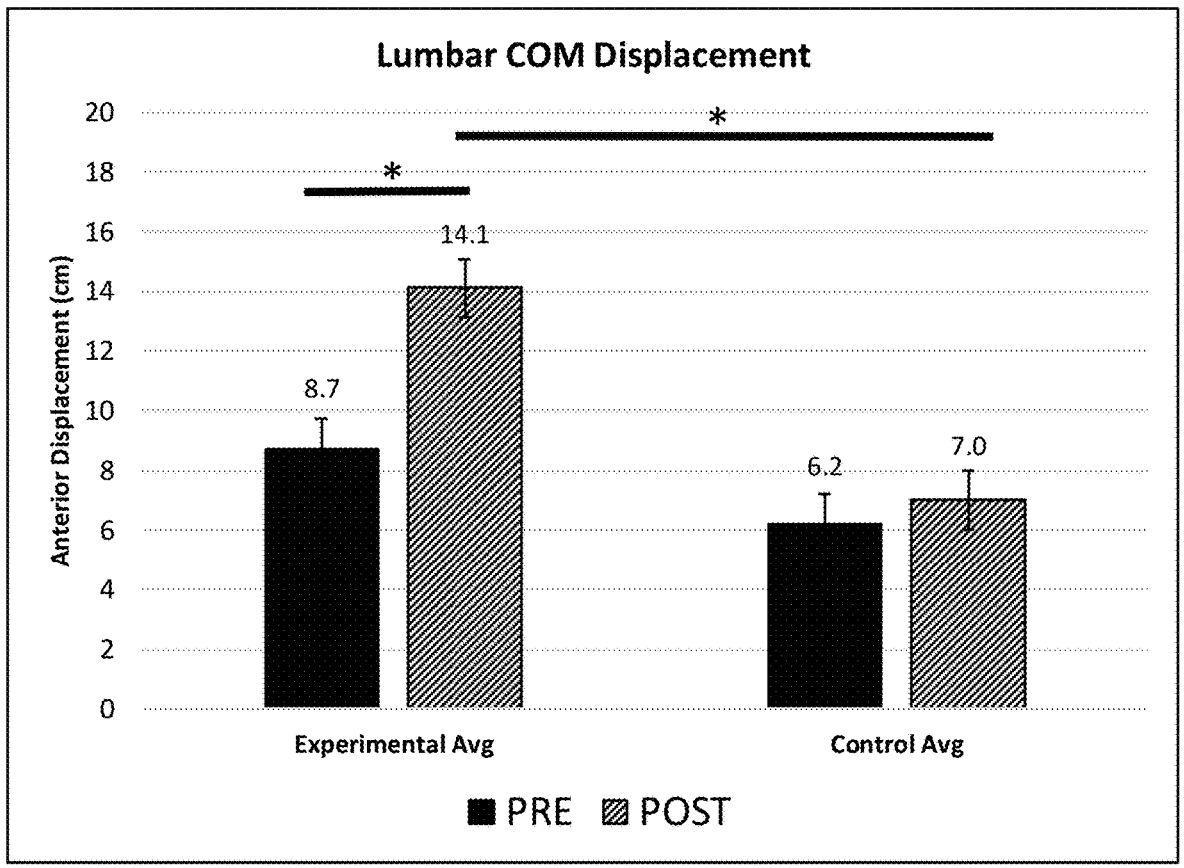
FIG. 6 shows lower trunk COM displacement, measured from the stable/neutral position to the failure point during the functional reaching task, pre and post training for the experimental and control group (*=p<0.001).

The anterior COM lower trunk displacement (e.g. position of belt) during the pre and post-training stages is depicted in FIG. 6.

The two groups started from a similar baseline in COM displacement (6.2 cm and 7.0 cm p=0.368). There was a significant Test Session X Group interaction (F=11.33(1.18), p=0.003, 0.2=0.89), with the pairwise comparison showing a significant increase of 61.4% in experimental subjects (p<0.001) compared to an increase of 14% in the case of controls (p>0.05) during the post-training. The results also indicated that a significant change in the rotatory component of both lower thorax and pelvis for the experimental subjects that received the training with the TruST.

Experimental results demonstrated that over a single training session, on an average, the subjects were able to significantly translate their body further anteriorly from their neutral postural configuration and significantly increase the rotational profiles of the lower trunk and pelvic segments in the flexion-extension plane of motion following the assist-as-needed force training with the TruST. Additionally, the subjects of the experimental group did not require frequent and long-lasting hand contact with the table during the training phase.

Figure 7:
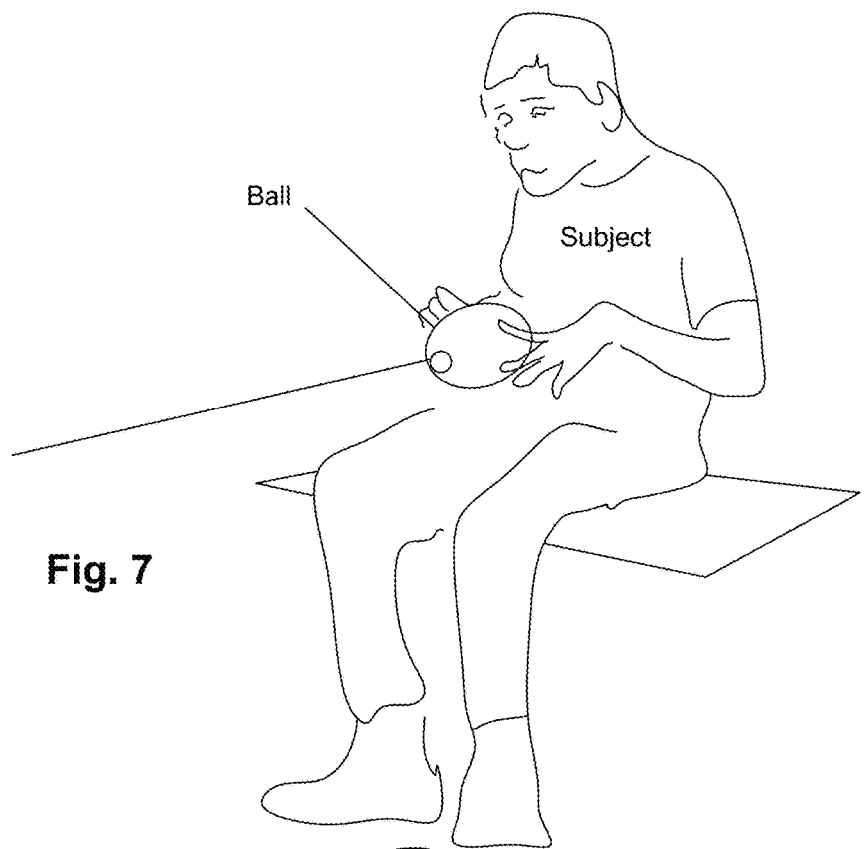
FIGS. 7 and 8 show neutral starting position and reach of anterior reach task to determine stability boundary for training.
Figure 8:
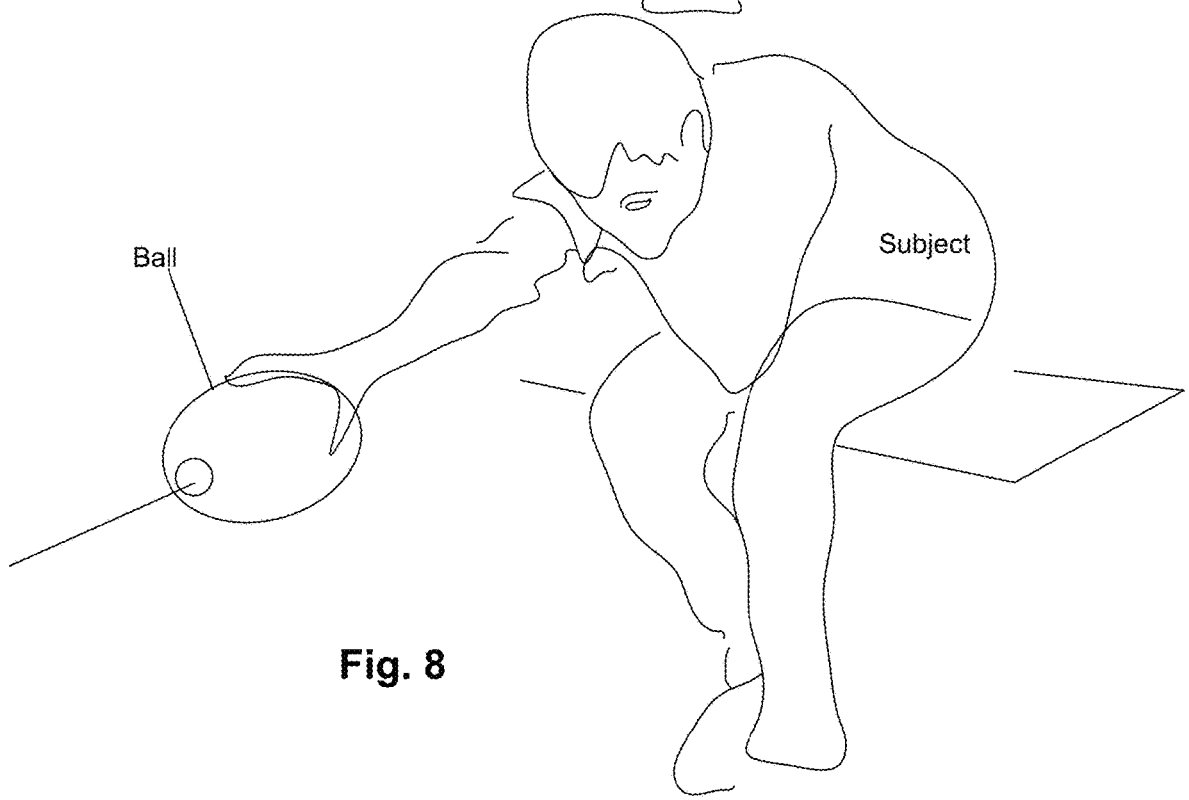

An analysis CP was performed with TruST for postural training of a child with Cerebral Palsy (CP), Gross Motor Function Classification System (GMFCS) IV. This population group is severely affected, with inability to maintain head and trunk postures or control leg and arm movements. The patients require manual or powered wheelchairs for ambulation. The participant in the study was a 13 year old boy with GMFCS score of IV. The boy presented with lateral head and torso drop due to lack of postural control. The training with TruST provides a function of improving the control of his upper body. The goal of the intervention was to improve postural control of the upper body, while reducing postural sway during challenging reaching tasks. See FIGS. 7 and 8.

Figure 9:
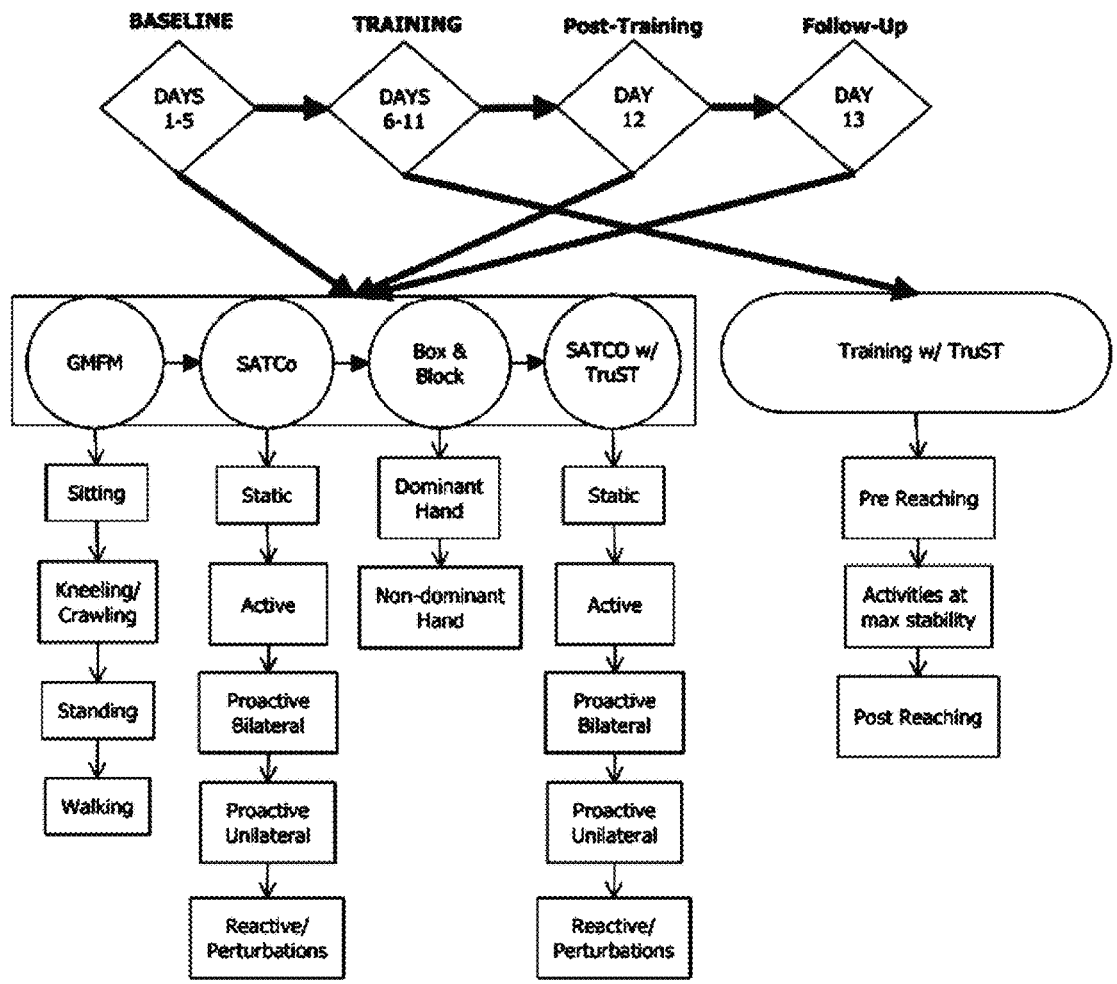
FIG. 9 shows a study protocol consisting of thirteen days of interaction with a subject identified with GMFCS IV in which the first five days were used towards pre-evaluations (baseline), six days for postural training, followed by a day of post-training evaluations and another day for a follow-up assessment.

Methods: The protocol consisted of thirteen days of interaction with the subject, as shown in FIG. 9.

The first five days were used towards pre-evaluations (baseline), six days for postural training, followed by a day of post-training evaluations and another day for a follow-up assessment.

A series of evaluations were conducted as a baseline to assess gross motor function using the GMFM scale, muscle spasticity using the Ashworth Scale, and trunk control using segment straps for safety. (i) Static: The patient was asked to sit with their hands raised for 20 seconds. (ii) Active: The patient was asked to follow an object with their head and eyes laterally to each side. (iii) Proactive Bilateral: The patient was asked to react quickly and accurately to grip a basketball with both hands. (iv) Proactive Unilateral: The patient was asked to hit a key on a toy keyboard, with a single hand at a time. (v) Reactive: The patient was asked to react to manual perturbations and to return to their stable/neutral configuration as fast as possible.

After completion of Segmental Assessment of Trunk Control (SATCo) (Butler et al. 2010), the subject performed a box and block test with each hand to assess dexterity in the hand and fingers. Finally, SATCo was repeated using the TruST as the segment control device. In this case, the trunk was fixed using static control with the motorized cables. The reactive tasks (perturbations) were conducted using quantitatively measured and administered forces to each side (anterior, posterior, and right and left lateral) of the subject. The perturbing forces were selected to be 25 percent of the body weight.

Prior to testing, the subject performed a reaching task, as shown in the figure above the last figure (photo of subject). The subject was asked to displace a ball on a string, as far as possible, while maintaining sufficient trunk control to return back to the neutral anatomical configuration. The TruST was used to create an assist-as-needed circular force tunnel around the measured border of stability. Within this region the patient can move freely and independently. Outside this region, an assistive force of 10 percent of body weight was applied to guide the patient back to the boundary of stability where he could regain independent control. With this, the patient can experience and explore new postural configurations while strengthening the postural muscles.

During training, the patient was asked to participate in a series of games that required reaching and manipulation, while maintaining trunk control. The tasks were performed at the boundary of stability defined by the force tunnel. These tasks were conducted for a total of two-hours. The reaching task (ball on a string) was conducted again to identify changes in the boundary of stability.

Post-Training: After six days of training, the baseline activities were re-performed to assess the changes in postural stability (by means of postural sway, translations, and rotations), GMFM, SATCo, and AbiliHand scores, and dexterity assessment.

Figure 10:
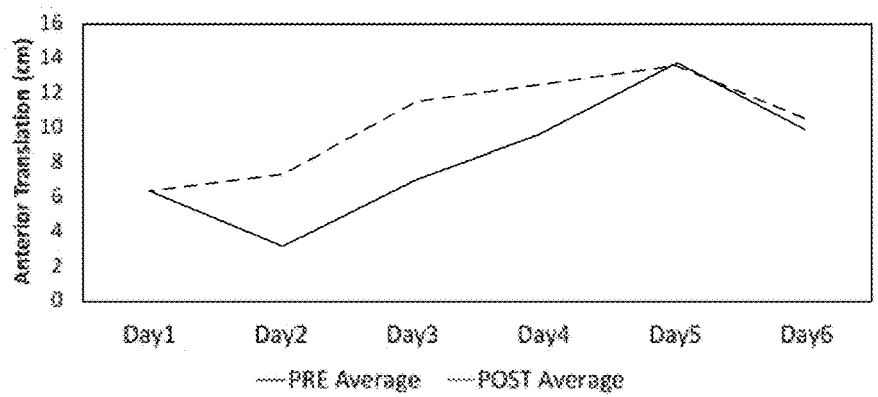
FIG. 10 shows the subject improved the boundary of stability, on an average, of 13.1% per day with an overall improvement of 111% in lower lumbar translation over the entire training period.

Results: The results indicated improvements in stability boundaries after each day of training. Specifically, the subject improved their reaching boundary, on an average, of 13.1% per day with an overall improvement of 111% in lower lumbar translation over the entire training period (FIG. 10). The subject was able to reach further from the center of his base of support (BoS) with each training session. It was visually evident that the patient sat further upright and was able to reach each of the lateral sides without using hand support for stability.

Each training session lasted for a total of two hours. The tasks were physically challenging, requiring the patient to perform varied and repetitive tasks at and past their boundary of stability. Evaluation of post-training translations of the lower lumbar segment showed fatigue, decreasing from the pre-training measurements by 20.8% on average. Yet, the translations increased each day and trended towards the pre-training translations, surpassing the pre-training value by 2% on day five of training. This indicates that besides stability training, TruST provided trunk strengthening and endurance training whereby on the fifth day of training, the patient was able to perform equally well in their pre and post training lower lumbar translation task, overcoming fatigue.

During post training assessment, the SATCo revealed increased stability at the lower lumbar region, which was not seen prior to training. The patient performed very well to perturbations, with minimal to no postural sway. At this point the pelvic straps were removed and the SATCo was repeated, showing successful progression of the training to a next trunk segment.

Studies with Pediatric SCI Patients: The following two studies, one experimental and the other clinical, indicate the preliminary work to develop and test therapeutic interventions and measurements focused on restoration of pre-morbid trunk control in pediatric-onset SCI. The first is the experimental Kids STEP Study and the second is clinically-based data from the Pediatric NeuroRecovery Program at Frazier Rehab Institute in association with the Christopher and Dana Reeve Foundation NeuroRecovery Network.

This specification describes the use of TruST for improving volitional trunk displacement for direction specific kinematic adaptation, through training with a novel challenging postural task conducted without foot support. Healthy adult subjects may be trained at their maximum trunk displacement or failure point in a VR environment and then compare with results in a real environment with physical objects, with and without the assist-as-needed forces of the TruST. A motion capture system was used to determine the subject's maximum seated lower trunk COM displacement and a force tunnel was created at that distance. During the experiment, subjects performed a total of five blocks of two trials each of a nine-hole peg test placed at the subject's point of stability failure, measured during the baseline stage. The study tests and supports the hypothesis that a single training session in a VR environment, at a maximum stability region, increases lower trunk COM displacement and shows similar outcomes as training in a real environment with physical object manipulation.

Figure 11:
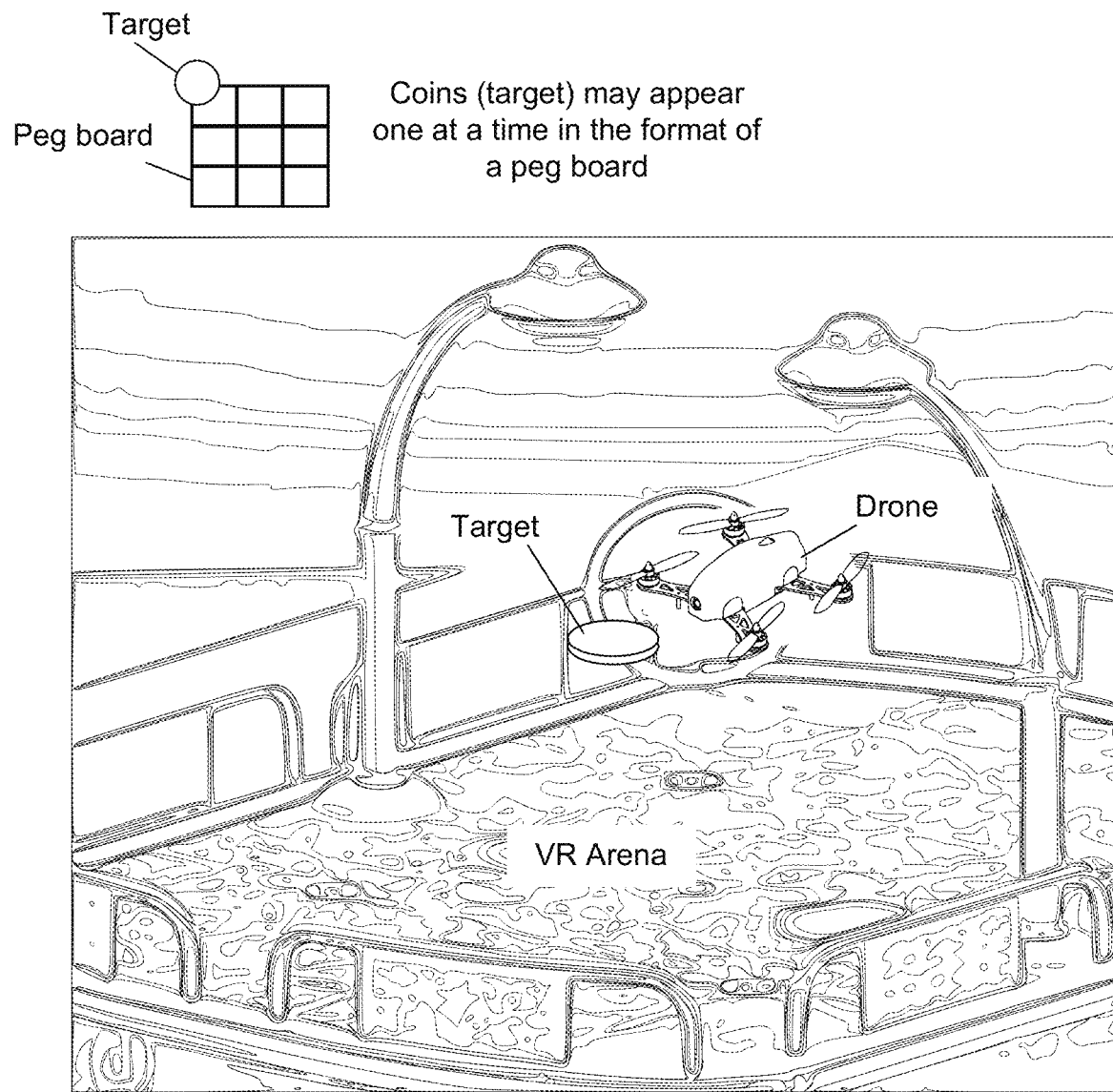
FIG. 11 shows the VR view of the VR gaming environment where the drone is controlled by the motion of the hand challenging the user to collect target (coins) at their individualized postural stability limit where a drone indicates the position of the real world effecter (hand).

FIG. 11 shows the VR view of the VR gaming environment where the drone is controlled by the motion of the hand challenging the user to collect target (coins) at their individualized postural stability limit where a drone indicates the position of the real world effecter (hand).

Figure 3:
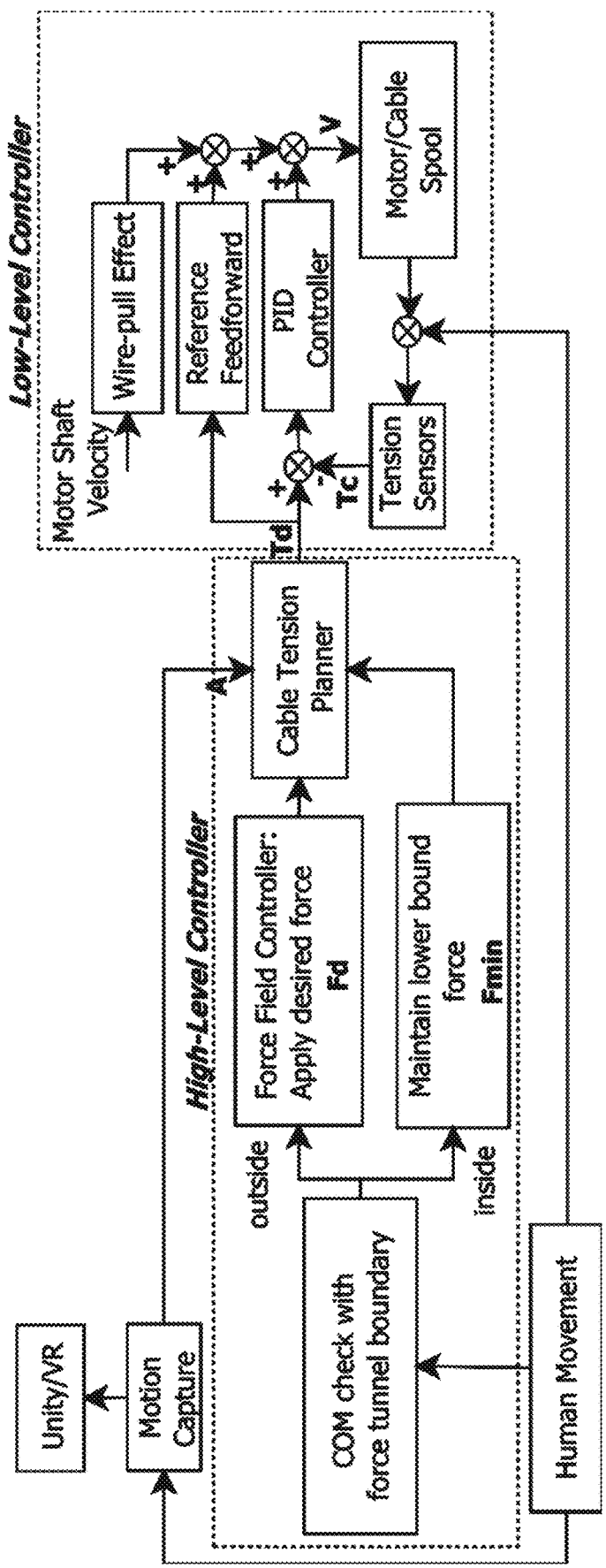
FIG. 3 shows a control system block diagram of the high and low level controllers, the high-level controller planning the desired cable tension vector Td to apply desired force/moment Fd, once the COM is outside the boundary and the low level controller implementing these tensions using a feedback PID loop, while the human hand motion is transmitted into Unity3D to control the VR gaming environment.

Referring to FIG. 3, the high-level controller plans the desired cable tension vector $T_d$ to apply desired force/moment $F_d$, once the COM is outside the boundary. The low-level controller implements these tensions using a feedback PID loop. The human hand motion is sent into Unity3D to control the VR gaming environment.

As indicated in FIG. 1, TruST utilizes four cables attached to each corner of an adaptable but rigid torso belt, while the other end of the cables are connected to AC servo motors attached to a fixed frame. The cable attachment points on the belt are reinforced with thermoplastic to eliminate belt deformation during force application. The motors have encoders (AKM series motors and AKD drivers from Kollmorgen, Pa.). A tension sensor (MLP-200 Transducer Techniques, California) and a spring (Stiffness 2.5 N/mm) are attached in series to each cable to measure the tension. These tension sensors record force up to 890N and are powered by a 12V DC amplifier (TMO-1 Transducer Technique, California). Pulleys are used to route cables from the motors to the torso belt along the transverse plane. A cable spool of 5 cm diameter is attached to the end of each motor shaft to prevent the cables from wrapping over themselves. A motion capture system (Bonita-10 series from Vicon, Denver) is used to record the cable attachment points on the belt and pulley to calculate the force directions. A two-stage control is implemented using LabVIEW, PXI real time controller and data acquisition cards (National Instrument, Austin). A VR headset (Oculus Rift, California) was used to display the virtual environment created in Unity3D (Unity Technologies, San Francisco, Calif.).

Four cables may be connected to each corner of the torso belt to apply the desired force/moment in the transverse plane. If tensions in the cables are represented by $T \in R^{4 \times 1}$ then the force-moment vector $F \in R^{6 \times 1}$ applied at the trunk segment can be obtained by:

$$F = AT \qquad (1)$$

where, $$F = [F_x F_y F_z M_x M_y M_z]^T \qquad (2)$$

and A is a 6×4 structure matrix based on the system. The matrix A can be expressed as:

$$A = \begin{bmatrix} \ldots & \vec{T}_i & \ldots \\ \ldots & r_i \times \vec{l}_i & \ldots \end{bmatrix}_{6 \times m} \qquad (3)$$

where $\vec{l}_i$ is the $i^{th}$ unit cable length vector away from the rigid body and $r_i$ is the vector from the center of the rigid body to the cable attachment point i on the rigid body.

FIG. 2 shows how the high-level controller assesses the spatial position of the estimated center of the trunk P such that once P is outside a specified radius (r), a normal force is applied to assist the subject back into the force tunnel and the large circle denotes the force tunnel, determined by the boundary of stability.

A quadratic programming based optimization scheme was implemented to solve Eq. (1). This is to minimize discontinuities in positive tensions T, often seen with linear programming, which finds the optimal solution at the corner of a convex hull of the feasible set. The objective function minimizes deviations between T and $T_p$ as follows.

$$\min f \quad (4)$$
$$f = \frac{1}{2}(T - T_p)^T (T - T_p)$$

such that, $$F_x = F_{dx}; F_y = F_{dy}$$

$$-25 < F_z < 25; -15 < M_{x,y,z} < 15$$

$$T_{min} < T < T_{max}$$

where $T_p$ is a positive tension value at the previous time instant, added to the objective function to ensure non-zero cable tension values. $T_{min}$ and $T_{max}$ are lower and upper bounds for the cable tension values. Inequalities were set to create upper and lower $F_z$, $M_x$, $M_y$, and $M_z$ boundaries which allow the solver to sufficiently solve for $F_x$ and $F_y$ forces within the inequality constraint. Since no movement about the BOS is purely planar, the solver solves for the specified planar forces $F_x$ and $F_y$, while the other DOF are constrained within the specified $F_z$, $M_x$, $M_y$, and $M_z$ boundaries. These were determined through testing prior to the study. The normal transverse force, $F_d = [F_{dx}\ F_{dy}]$, is computed by the high-level controller discussed in the next section.

Figure 4:
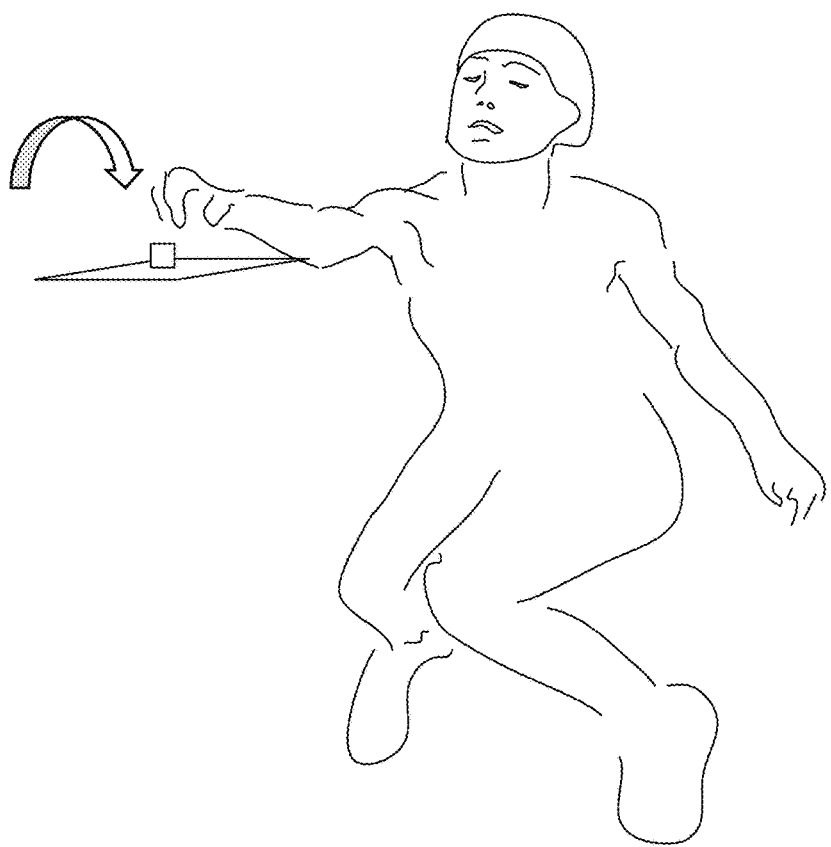
FIGS. 4 and 5 show a nine-hole peg test and a modified functional reach test, respectively, that were performed during a human experiment.
Figure 5:
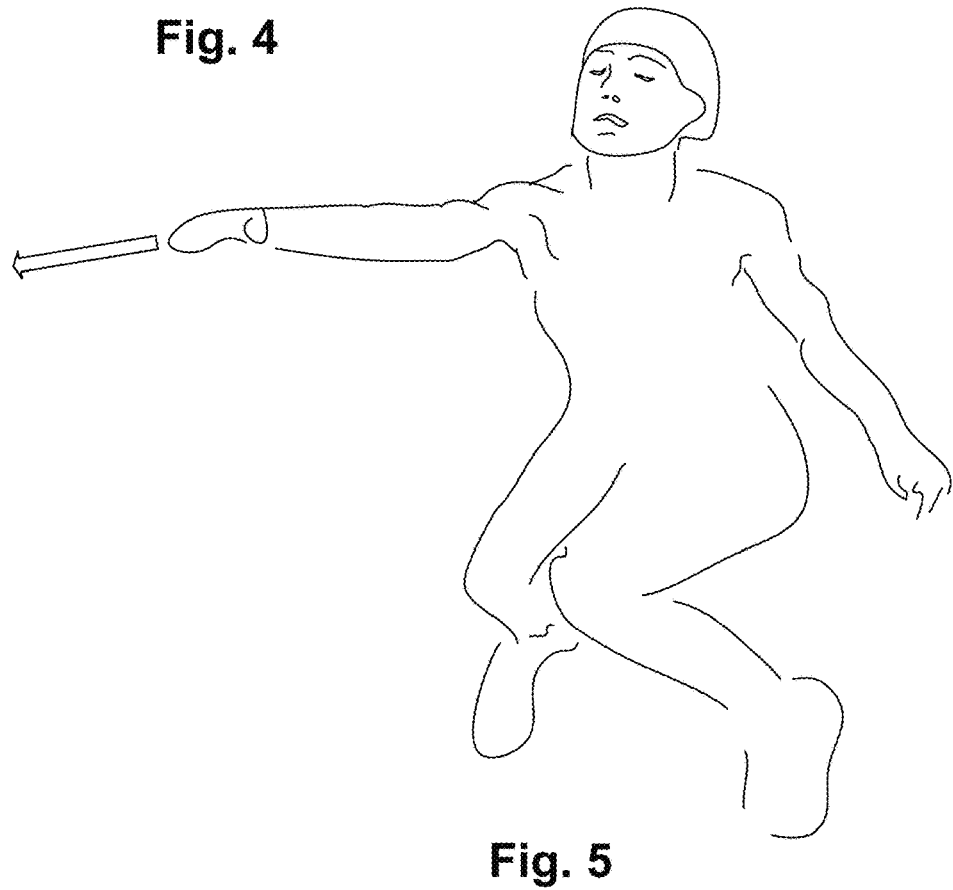

The high level controller consists of a force tunnel controller, which creates a virtual force field at a specified radius around the subject's trunk in the transverse plane. The center of the lower trunk is obtained by using a motion capture system and computing the estimated centroid of the left and right lateral points on the belt. The controller is designed such that when the trunk center is outside the specified circle of radius r, normal forces are applied to provide guidance to the center point back inside the circle, into a region of trunk stability (FIG. 4).

Let P be the current position of the trunk centroid, $P_1$ and $P_2$ be the two closest predefined points to P along the circular force tunnel with radius r. P' be the point perpendicular to P on the line between $P_1$ and $P_2$, with the force magnitude k.

$$F = F_n = k(\vec{n}) \quad (6)$$

where the direction of the force, $\vec{n}$ is found by:

$$\vec{n} = \frac{(P' - P)}{\|P' - P\|} \quad (7)$$

and the perpendicular point P' as, $$(P_1 - P_2) \cdot (P - P') = 0 \quad (8)$$

$$P' = (1 - m)P_1 + mP_2 \quad (9)$$

where, $$m = \frac{(P_1 - P_2) \cdot (P_1 - P)}{\|(P_1 - P_2)\|^2} \quad (10)$$

The force constant k was found by trial and error, prior to the experiment. During the study, it varied between training blocks, decreasing from 60N (block 1) to 52N (block 5). This was chosen through trial and error prior to testing to ensure adequate assistive force, with a noticeable decrease through training blocks.

C. Low Level Controller:

The low-level controller runs at 1 k Hz using LabVIEW PXI real time controller. An open loop feed forward term $T_{FF}$ and a closed loop PID based feedback term $T_{FB}$ are implemented to achieve the desired tension. The voltage provided to the motors yields $$V = K_M (T_{FF} + T_{FB}), \quad (5)$$

where $K_M$ is a pre-measured motor constant, which is obtained from a linear relation between voltage and desired tension for each motor.

D. VR System:

The VR gaming environment consists of a drone and a coin collecting gaming task. Coin location is specified by user input and the drone is controlled by hand motion, communicated through Vicon motion capture cameras to Unity3D software. The environment is projected in a three-dimensional form inside an Oculus Rift headset.

Ten additional healthy adult subjects (Avg: 25.7 yrs/155 lbs/174 cm, 7 male, 3 female, 9 right-handed and 1 left-handed) were recruited for the VR group and compared to a previous twenty healthy adult subjects (20-30 yrs, 12 males, 8 females, 19 right-handed, and 1 left-handed) who were recruited and randomly assigned to either the physical environment training/reality (PR) or control group. Before training, subjects were instructed about the training protocol. The PR and control group were randomly assigned and were not told which group they were in. The VR group was aware of their group as they had to wear a VR headset. Retro-reflective markers were placed on the subject to record kinematics using a Vicon motion capture system. The subjects were seated on a stool at the center of the TruST. An adaptable but rigid three-inch wide belt was attached to the lower trunk (lumbar) region.

The training activities were separated as PR training using a nine-hole peg task or VR training using a virtual coin collecting game task structured in the same format (collecting nine coins spaced out at the same distance as the peg board). The peg board has 3×3 holes of 4 mm diameter and the subject is instructed to pick a peg from their dominant side and place it into the peg board. For the VR group, to simulate the same training in a virtual environment, the subject is instructed to touch a button on their dominant side before collecting the coins spaced in a 3×3 configuration at 4 mm apart.

During the BL, the pre-training tasks consisted of the functional reach test to determine the maximum lower trunk displacement and define the point of stability failure for all three groups. The PR and control groups conducted a pre-training nine-hole peg task without assistive forces, while the VR group conducted the virtual coin collecting game task with no assistive force. During the T stage, five blocks of two consecutive trials of the nine-hole peg task was conducted for the PR and control group, while the VR group performed the virtual coin collecting game task. This was followed by PT stage in which both, functional reach and nine-hole peg tasks for the PR and control group and functional reach and virtual coin collecting task for VR group, were re-assessed after removing the external assistance from TruST.

During the experiment, all subjects were asked to sit on a flat, wooden stool. The torso belt was firmly placed at the lower trunk. The subjects were asked not to use any foot or hand support while performing the functional reach task and the nine-hole peg task. However, they were allowed to move their body freely as desired, to complete all tasks to the best of their ability. All tasks started from a stable neutral position with the head and trunk centered over the pelvis, with elbows in external rotation and bent 90-degrees in the air. Subjects were instructed to perform each task as fast and accurately as possible, while maintaining postural control. During training, subjects were allowed to use a finger or the volar area of the wrist for support on the table, only if posture stability was lost during the placement of the pegs.

For the functional reach test, the subjects were asked to displace a wooden block anteriorly as far as they could in a controlled and self-paced manner. If the subject used any support or lost balance, the task was stopped and the point of stability failure was kinematically recorded. If the subject lost balance prematurely, they were allowed to repeat the task. Premature loss of balance was indicated if 1) the subject touched the table surface for support, or 2) there was premature foot-ground contact for displacing the piece of wood at further distance.

The reach test was performed at BL and PT, with the shoulders flexed at 90-degrees and arm parallel to the floor. The failure point was used to identify the boundary of postural stability. This boundary specified the maximum anterior translation of the lower trunk before postural collapse.

For the PR and control group, the nine-hole peg board was then placed in front of the subject. The furthest row of the board was positioned in line with the position of the wooden block where the stability failure happened during BL. For the VR group, the coin position was set to the wooden block position, or the stability failure point. The subjects were instructed to grab a peg from their dominant arm and to place it onto the board from the dominant side to opposite side, working from the closest row to the furthest. For VR group, the subjects were instructed to touch a button at their dominant side and then reach to grab the coins, as these appeared one at a time in a specific order, from the dominant to opposite side and closest to furthest away.

The coins also ranged in color from bronze, silver, and gold, to identify from closest to furthest in distance. After inserting the nine pegs, subjects removed these in the same order, while the VR group recollected the coins in the same order. A complete cycle of inserting and removing pegs or collecting coins twice was identified as a single trial. Two consecutive trials conducted at a time were defined as a block. Five blocks were conducted, with the assist-as-needed, error based force for the VR and PR group at or beyond the predefined maximum lower trunk displacement (e.g. point of stability failure). Accordingly, the subjects moved independent of any assistance as long as they were inside the force tunnel but received assistance at and beyond their failure point. The assistive force was decreased by 2N (3.33%) after each block of training. The subjects were allowed as much rest time as they needed between sessions to a maximum of five minutes. The same protocol with the peg board was followed for the control group but no assistive forces were provided.

Figure 12:
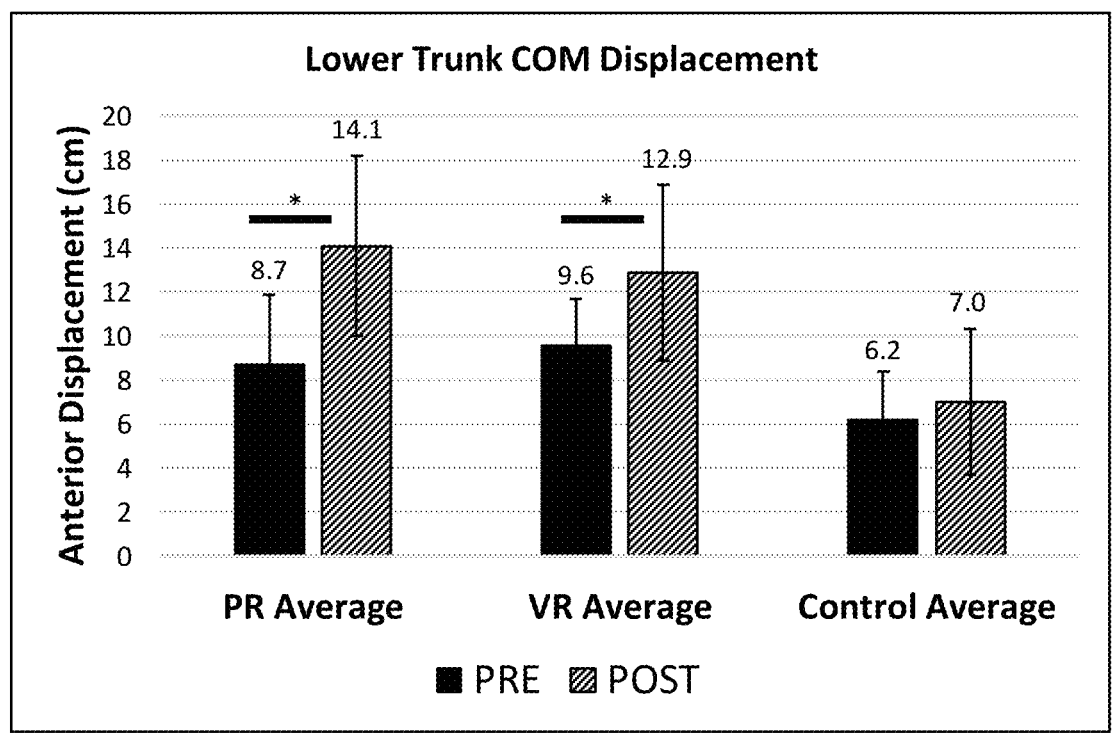
FIG. 12 shows lower trunk COM displacement, measured from the stable/neutral position to the failure point during the functional reaching task, pre and post training for the PR, VR, and control group (*=p<0.005).
Figure 13:
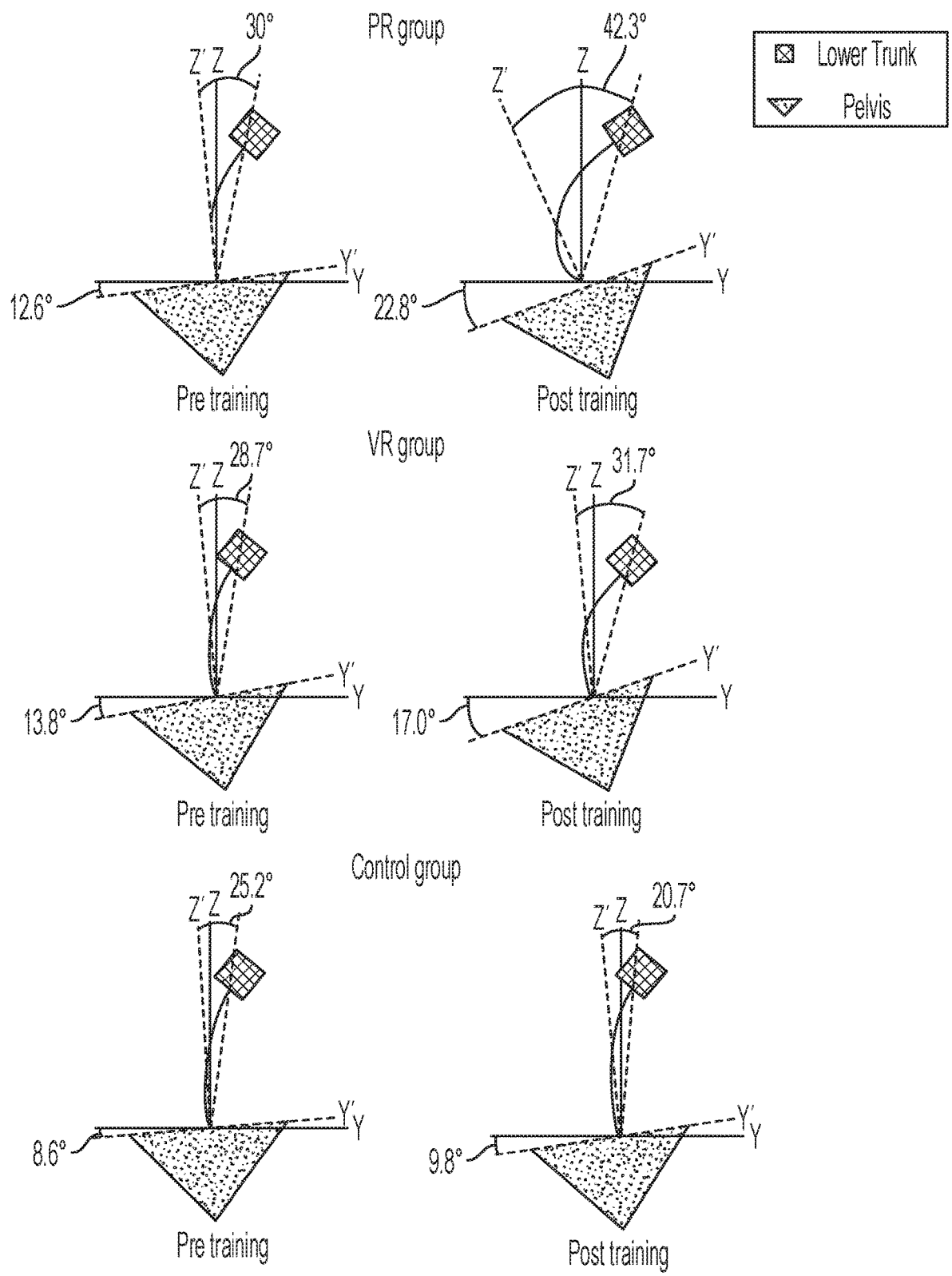
FIG. 13 shows lower trunk and pelvis schematic indicating the average rotation in the anterior/posterior direction, pre and post training for the PR, VR, and control group.
Figure 14:
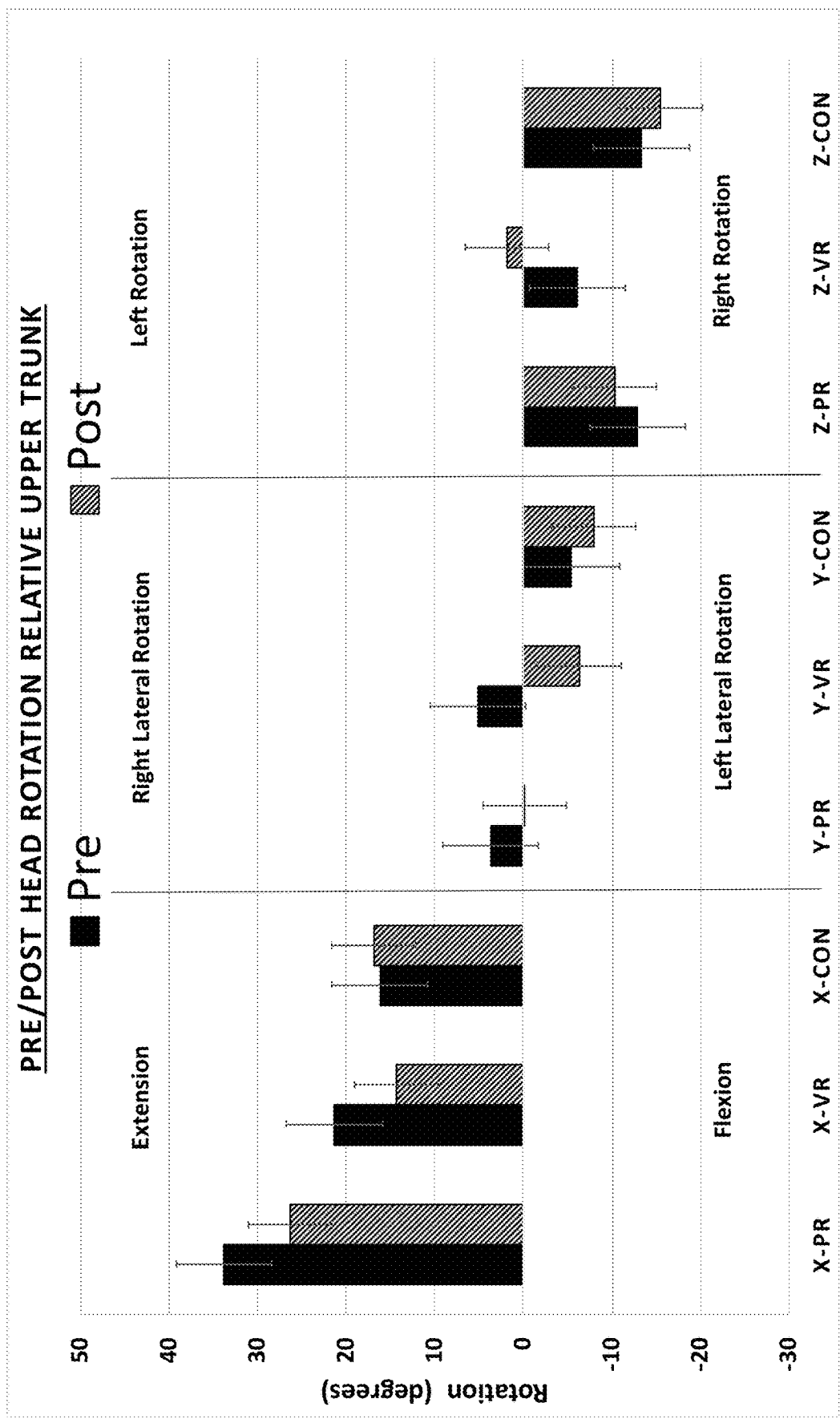
FIG. 14 shows pre and post head rotation relative to the upper trunk, for the experimental and control groups (in degrees).
Figure 15:
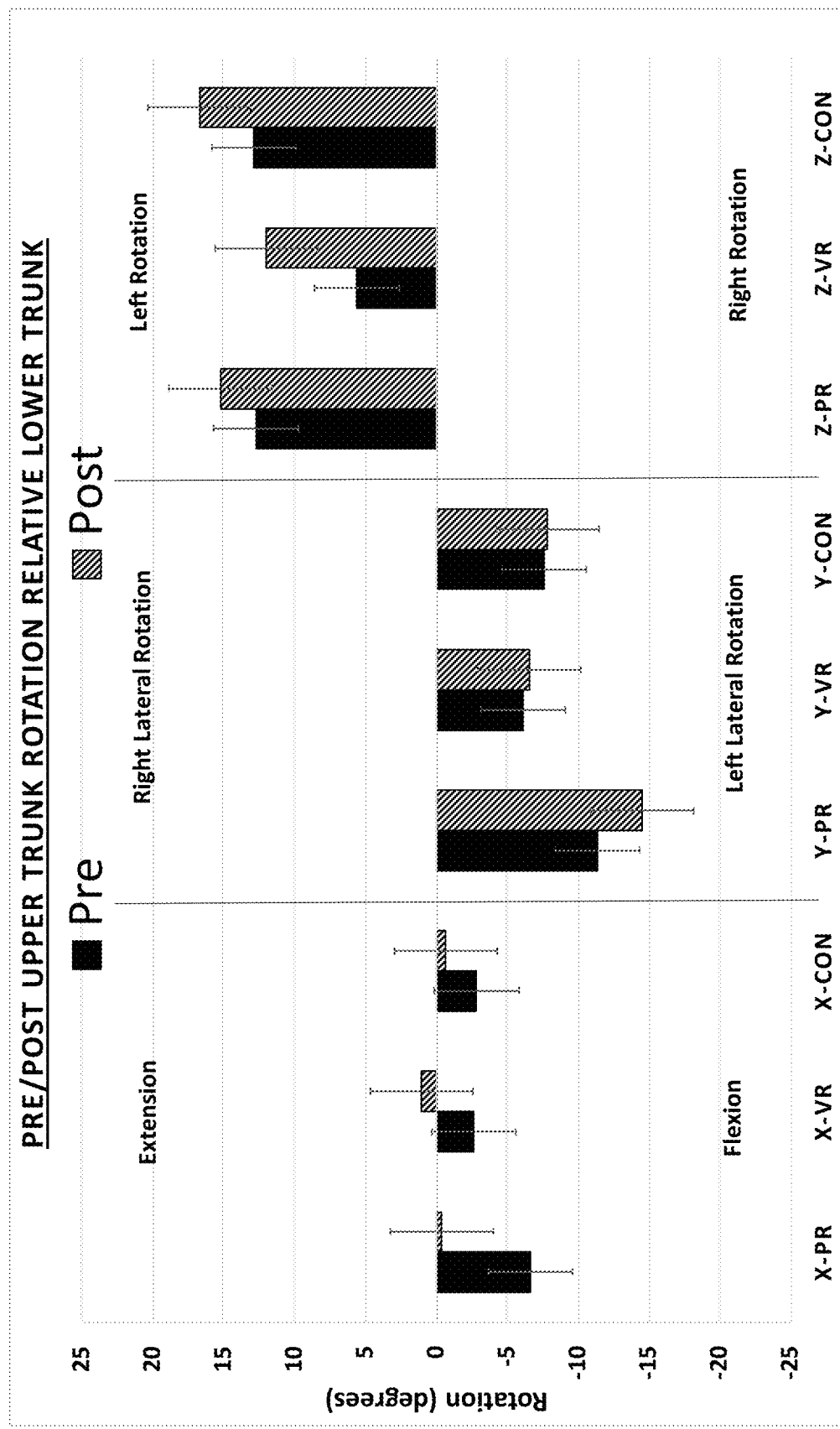
FIG. 15 shows pre and upper trunk rotation relative to the lower trunk, for the experimental and control groups (in degrees).

FIG. 12 shows lower trunk COM displacement, measured from the stable/neutral position to the failure point during the functional reaching task, pre and post training for the PR, VR, and control group (*=p<0.005). FIG. 13 shows lower trunk and pelvis schematic indicating the average rotation in the anterior/posterior direction, pre and post training for the PR, VR, and control group. FIG. 14 shows pre and post head rotation relative to the upper trunk, for the experimental and control groups (in degrees). FIG. 15 shows pre and upper trunk rotation relative to the lower trunk, for the experimental and control groups (in degrees).

Figure 16:
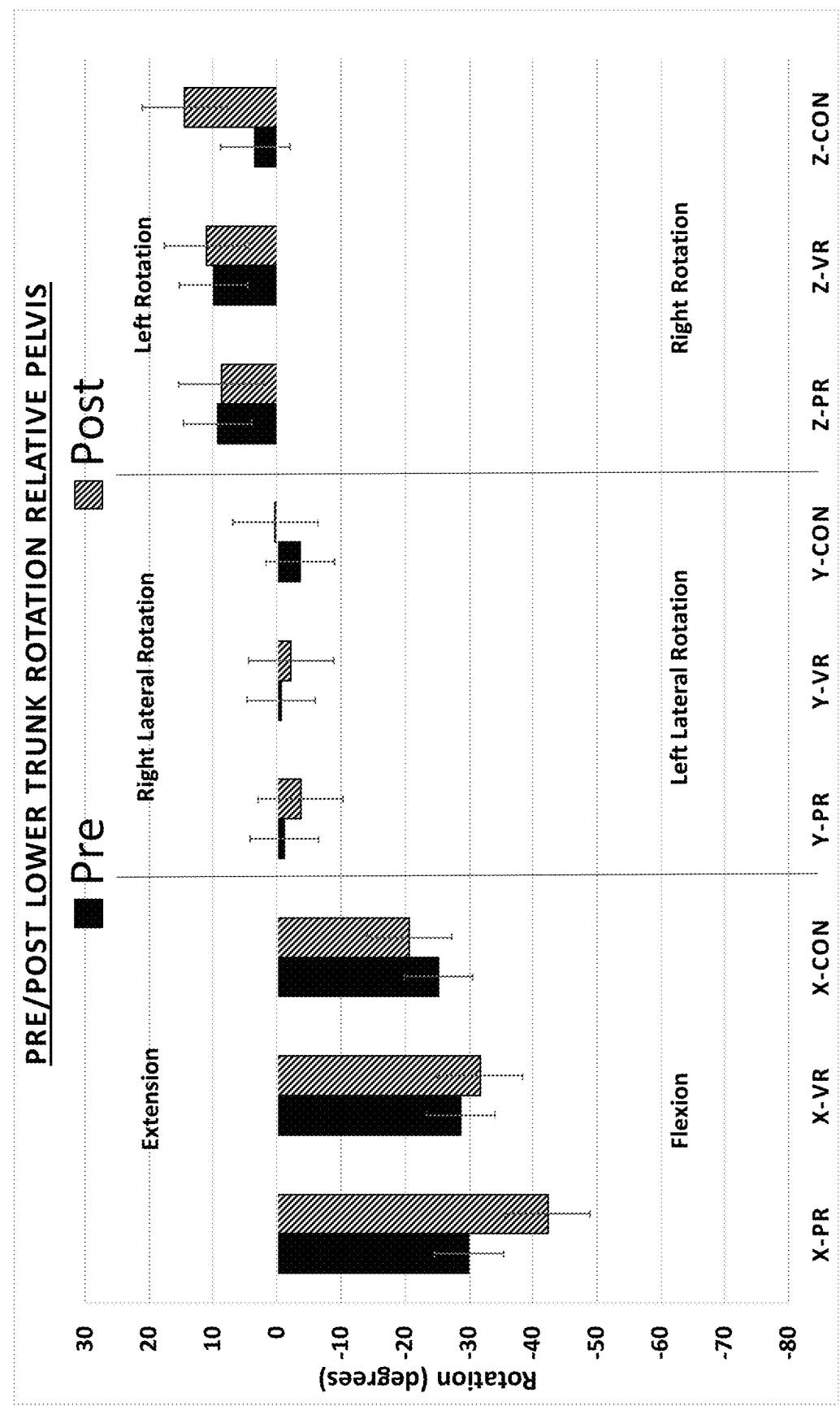
FIG. 16 shows pre and post lower trunk rotation pelvis for the experimental and control groups (in degrees).

The data were analyzed to assess the spatiotemporal changes in head, upper trunk, lower trunk, and pelvis translation and rotation between pre and post functional reach test between the VR, experimental, and control group. The data were analyzed using MATLAB (MathWorks, Natick). The COM of the lower trunk was estimated using right and left belt markers. Translation of this trunk segment was measured in the anterior-posterior direction, from start of the trial (neutral position) to the point of stability failure. The statistical analysis was conducted using SPSS 23 (SPSS, Chicago, Ill.). A two-factor mixed-design ANOVA was conducted with one within factor (Two Groups: Pre-Training and Post-Training) and one between factor (Three Groups: VR, PR, Control). Pairwise comparisons are reported if the interaction was significant and p values were adjusted using Bonferroni's procedure. The alpha value was set at 0.05 for both statistical procedures. FIG. 16 shows pre and post lower trunk rotation pelvis for the experimental and control groups (in degrees).

The anterior COM lower trunk displacement (e.g. position of belt) during the pre and post-training stages is depicted in FIG. 13. There was a significant Test Session X Group interaction (F=4.47(2.27), p=0.021, $\eta^2$=0.72), with the pairwise comparison showing a significant increase of 61.4% in the PR group (p<0.001) and 34.4% in VR group (p=0.004) compared to an increase of 14% in the case of controls (p>0.05) during the post-training. Both PR and VR showed significantly more range of motion in translations compared to the control, 515% (p=0.001) and 278% (p=0.006) respectively, while there was no significant difference between the PR and VR group (p>0.05).

The changes in head, upper trunk, lower trunk, and pelvis rotations are shown in FIGS. 13-17. The pelvis rotation was measured relative to the global frame, while each segment was measured in relation to its caudal segment (e.g. the upper trunk relative to the lower trunk). There was a significant Test Session X Group interaction for lower trunk (F=3.41(2.27), p=0.048, $\eta^2$=0.59) and pelvic rotation (F=5.37(2.27), p=0.011, $\eta^2$=0.80) in the flexion/extension axes (FIG. 13). These results indicate a significant increase in the rotatory component of both lower thorax (FIG. 10) and pelvic rotation (FIG. 11) for the PR group compared to the control, with a tendency of interaction effect for pelvic rotation (p=0.056) between the VR and control group.

Specifically, after training, lower trunk rotation increased towards flexion by 41.3% (p<0.001), while pelvic rotation increased towards extension by 81.0% (p<0.001) for the PR group. However, the VR group showed an increase toward flexion 10.5% (p=0.516) and a pelvic rotation increase towards extension by 23.5% (p=0.123). There was no significant change in the control group (p>0.05) and no interaction effect between the PR and VR group.

It was determined if specific practice of a seated reaching task (without foot support) in a virtual environment, at and beyond the individual's point of postural stability failure, could enhance volitional control of upper body and extend the stability limits established by the configuration of the pelvis. The results were compared with experiments conducted in a real environment with physical object manipulation and with a control group to extract the advantages of a VR based training. Experimental results demonstrated that on average, over a single training session the subjects were able to significantly translate their body further anteriorly from their neutral postural configuration with both physical reality and virtual reality training, while physical reality training also significantly increased the rotational profiles of the lower trunk and pelvic segments in the flexion-extension plane of motion following the assist-as-needed force training with the TruST. On the other hand, the control group (reality training without assist-as-needed forces) did not show any significant change.

The significant increase in anterior lower trunk translation seen with the PR and VR group, but not with the control group demonstrate that the TruST robotic system has a significant beneficial effect in seated posture training. The assist-as-needed force strategy allows the subjects to train at their maximum stability limits without failing. This allows the subject to explore a larger range of motion and a stable postural configuration required to maintain or recover seated balance. On the other hand, the control group does not get enough time to spend at the stability boundary without failing and thus have to use their hand for support. As a result, the sensorimotor postural experience required for adjusting their postural kinematics to complete the task successfully may be decreased compared to the PR and VR group who were provided with the assist-as-needed force from TruST. Furthermore, it was visually apparent that the control group had difficulty maintaining dynamic postural stability during the peg board test at positions beyond their stability limits. In this case, the subject repetitively had to place their fingers for support while the PR group showed more consistency in their reaching, without often using the hand for support. Accordingly, the VR group did not have a table for support, as the experiments were virtual, and rarely placed their hands on the stool to regain stability during training.

In comparing the PR and VR groups, to observe the difference between training requiring physical object manipulation or through a gaming experience, it was seen that the reality based training produced slightly better outcomes. While both PR and VR groups showed significant increases in lower trunk translation, only the PR group showed significant increases in lower trunk and pelvic rotational profiles, while the VR group showed non-significant increases. This suggests that although both PR and VR training showed significant increases in postural range of motion, physical training can potentially show better outcomes. The training effect with the TruST showed that the pelvis increased towards extension while the lower trunk increased towards flexion, but only the changes in the PR group were significant. As stated by Nikolai Bernstein's theory of motor learning, the central nervous system's (CNS) hierarchy of control mechanisms for posture and movement are organized with distributed and parallel processing. Neural mechanisms that integrate posture with dexterity movements (e.g. reaching control) are distributed in the CNS and are recruited in patterns that are task oriented. By providing an assistive force at an individual's point of postural stability failure, the subjects experienced larger upper body displacements, and were better able to integrate the postural requirement within the context of the specified task. As the task was practiced at the point of stability failure or maximum level of stability, the subjects released the segmental in-block mode of control, in which the degrees-of-freedom are constrained, and increased their range of motion.

The improvements in seated postural range of motion were assessed with the use of an assist-as-needed force strategy from TruST, in a virtual and real training environment. For this reason, the virtual gaming experience was made to be less variable, and more repetitive in nature to mimic the training provided by a nine-hole peg test. Although controlling a drone and collecting coins add a gaming experience, the task can be seen as repetitive where a user can master the motion and timing required to successfully complete the training. For this reason, the level of cognitive engagement desired for a game based training may be diminished, leading to fewer improvements in outcomes as seen with the rotational profiles for the VR group. On the other hand, physical training such as the peg board, require adequately completing and witnessing an outcome (e.g. peg going into a hole) that feeds on visual and tactile stimulus, which might have led to an increased range of translational and rotational motion.

The main advantage that a VR can provide is variability of training. With variation of training, the cognitive demand and engagement is increased, as the user is required to make decisions under time constraints and possibly rewarded for improving through a scoring system. It maybe that due to a lack of variability in the training task in the VR group, the outcomes were not as large as those seen with the PR group. Yet, there was no significant interaction or difference between the PR and VR group.

Even though the improvements are significant only in translation and not rotation, VR training can be appreciated for its trade-offs. Although physical training would suggest a better outcome, VR training could be performed more readily without the need for added personnel, be more cost effective, and be extended to higher variability in training and in a low-cost environment, while physical (PR) training requires specific hardware and personnel for training. VR training can also be conducted at home and therefore can be done more often than PR training. It may be that more sessions of training can show far better improvement than a more challenging training conducted with fewer sessions. Another advantage of VR is that it can create direction specific, task oriented trajectories for training and modify the training task according to the subject's spatial position, recorded by a motion capture system. By using a virtual environment, it can adapt the difficulty of the training session progressively, challenging the subject and increasing the cognitive demand to complete the task successfully. This can be tested in future studies.

The differences between reality and virtual reality are presented based training in an active seated posture training device, TruST. The results were compared to a control group to identify the benefits of the assist-as-needed force strategy towards increasing seated postural range of motion. Postural stability is defined as the ability to displace the estimated COM of the lower trunk segment further from the neutral postural configuration of reference without postural collapse of the upper body. The results demonstrate that both virtual reality and physical reality based trainings, with assistive forces at and beyond the point of stability failure, enhance volitional control of seated trunk displacements. These outcomes follow motor learning theories where a challenging task oriented training can recruit and release the DOF to organize postural kinematics. In addition, the trade-off between reality and virtual reality training is shown, where VR training could be performed more readily, be cost effective, be more cognitively engaging due to its game like nature, and provide variability in training at ease and in a low-cost environment, while physical training requires specific hardware and personnel for training. The system may also be used to analyze, and treat based on, the changes in seated postural kinematics during game based variable tasks and the effect of VR posture training with TruST in patient populations.

Seated postural control requires the stabilization and control of the head and trunk to complete many daily tasks, e.g., reaching for an object beyond maximum arm's length.

Although sitting statically upright can be less demanding with the center of mass (COM) of the upper body centered over the base of support (BOS), large and quick displacements of the upper body outside the pelvic boundaries can cause a sudden shift of the COM away from the center of the BOS, creating a lack of a stable neutral upper body and pelvic position. This will be particularly true when the contact between foot soles and ground is reduced or eliminated. In this situation, high volitional control of the upper body is required to recover verticality and maintain stability.

While healthy individuals can readily perform everyday activities, such as leaning, reaching, and grasping, patients with neurological and musculoskeletal disorders (MSDs) may have control deficits in shifting their weight and moving their upper body within and beyond the pelvic boundaries in the seated position without losing stability and balance. These tasks are neurologically demanding requiring the primary motor cortex, somatosensory systems, and frontal and parietal areas to play an essential role to maintain balance. Coordination between the occipito-parieto-frontal reaching and grasping circuits and the cortical-sub-cortical postural systems must occur. The musculoskeletal postural framework acts to resist gravitational forces and internal and external disturbances during motor tasks in addition to provide mechanical support and balance. The postural control can be divided into two functional levels: generation of direction specific kinematic movements and adaptation of these specific movements on the basis of multi-sensorial afferent inputs. Studies have shown that direction specificity emerges as a result of self-organization of intersegmental components during exposure to new positions. Therefore, performing a new or more difficult task can show task-specific kinematic adaptations of posture. Postural control requires stabilization of all linked segments of the body through complex coordination of biomechanical, sensory, motor, and central nervous system components.

In the present embodiments, the use of TruST is described for improving volitional trunk displacement for direction specific kinematic adaptation, through training with a novel challenging postural task conducted without foot support. Healthy adult subjects are trained at their maximum trunk displacement or failure point. A motion capture system was used to determine the subject's maximum seated lower trunk COM displacement and a force tunnel was created at that distance. During the experiment, subjects performed a total of five blocks of two trials each of a nine-hole peg test placed at the subject's point of stability failure, measured during the baseline stage. The study tests and supports the hypothesis that a single training session at a maximum stability region increases lower trunk COM displacement and lower trunk and pelvis rotation.

The TruST may have motors with encoders (AKM series motors and AKD drivers from Kollmorgen, Pa.). A tension sensor (MLP-200 Transducer Techniques, California) and a spring (Stiffness 2.5 N/mm) are attached in series to each cable to measure the tension. These tension sensors record force up to 890N and are powered by a 12V DC amplifier (TMO-1 Transducer Technique, California). Pulleys are used to route cables from the motors to the torso belt along the transverse plane. A cable spool of 5 cm diameter is attached to the end of each motor shaft to prevent the cables from wrapping over themselves. A motion capture system (Bonita-10 series from Vicon, Denver) is used to record the cable attachment points on the belt and pulley to calculate the force directions. A two-stage control is implemented using Labview, PXI real time controller and data acquisition cards (National Instrument, Austin).

For the cable-driven systems, to keep tension in the cable $(T_{FF}+T_{FB})>0$, the lower bound of the feedback term is set as $T_{FB,low}=-T_{FF}$. However, if the subject pulls the cable away from the motor, extra negative input is required to compensate motor friction and unspool the cable reel. Only for this pulling case, the controller decreases the lower bound of the feedback term respect to the speed of the cable reel.

A representation of the desired and actual Cartesian force can be seen in FIG. 15. The PID controller was able to follow the desired force trajectory with a root mean square error of 6.89N (3.6%) with standard deviation of 6.38N. The min error was $6.61 \times 10^{-5}$N and max error 40.64N while any error above 10N lasted for a maximum of 0.135 s, due to a small delay in real time response.

Twenty healthy subjects (20-30 yrs, 12 males, 8 females, 19 right-handed, and 1 left-handed) were recruited and randomly assigned to either the experimental or control group. The training protocol was approved by Columbia University's institutional review board and consisted of three stages: baseline (BL/pre-training), training (T), and post-training (PT). Before training, subjects were instructed about the training protocol, but were not told whether they were in the control or experimental groups. Retro-reflective markers were placed on the subject to record kinematics using a Vicon motion capture system. The subjects were seated on a stool at the center of the TruST. An adaptable but rigid three-inch wide belt was attached to the lower trunk (lumbar) region. During the BL, the pre-training tasks consisted of the functional reach test to determine the maximum lower trunk displacement and define the point of stability failure, and a pre-training nine-hole peg task without assistive forces. During the T stage, five blocks of two consecutive trials of the nine-hole peg task was conducted (massed practice). This was followed by PT stage in which both, functional reach and nine hole peg tasks, were re-assessed after removing the external assistance from TruST.

During the experiment, all subjects were asked to sit on a flat, wooden stool. The torso belt was firmly placed at the lower trunk. The subjects were asked not to use any foot or hand support while performing the functional reach task and the nine-hole peg task. However, they were allowed to move their body to complete all tasks to the best of their ability. All tasks started from a stable neutral position with the head and trunk centered over the pelvis, with elbows in external rotation and bent 90-degrees in the air. Subjects were instructed to perform each task as fast and accurately as possible, while maintaining postural control. During training, subjects were allowed to use a finger or the volar area of the wrist for support on the table, only if posture stability was lost during the placement of the pegs.

For the functional reach test, the subjects were asked to displace a wooden block anteriorly as far as they could in a controlled and self-paced manner. If the subject used any support or lost balance, the task was stopped and the point of stability failure was kinematically recorded. If the subject lost balance prematurely, they were allowed to repeat the task. Premature loss of balance was found if 1) the subject touched the table surface for support, or 2) there was premature foot-ground contact for displacing the piece of wood at further distance.

The reach test was performed at BL and PT, with the shoulders flexed at 90-degrees and arm parallel to the floor.

The failure point was used to identify the boundary between postural stability and instability. This boundary specified the maximum anterior translation of the lower trunk before postural collapse.

The nine-hole peg board (3×3 holes of 4 mm diameter) was then placed in front of the subject, with the furthest row being in line with the position of the wooden block at the time of stability failure. The subjects were instructed to grab a peg from their dominant side and to place it onto the board from right to left, working from the closest row to the furthest. After inserting the nine pegs, subjects removed these in the same order. A complete cycle of inserting and removing pegs was identified as a single trial. Two consecutive trials conducted at a time were defined as a block. Five blocks were conducted, with the assist-as-needed, error based force for the experimental group at or beyond the predefined maximum lower trunk displacement (e.g. point of stability failure). Accordingly, the subjects moved independent of any assistance as long as they were inside the force tunnel but received assistance at and beyond their failure point. The assistive force was decreased by 2N (3.33%) after each block of training. The subjects were allowed as much rest time as they needed between sessions to a maximum of five minutes. The same protocol was followed for the control group but no assistive forces were provided.

The data were analyzed to assess the spatiotemporal changes in head, upper trunk, lower trunk, and pelvis translation and rotation between pre and post functional reach test. As exploratory performance measures, the percentage of time the experimental subjects required assistive forces provided by TruST and postural behavior of subjects during the T stage were analyzed. This last variable was assessed as the number of times the subjects would require 1) foot/reaching support due to postural collapse or 2) hand-table support for more than 1000 ms due to lack of upper body stability and/or inability to recover postural verticality.

The data were analyzed using Matlab (MathWorks, Natick). The COM of the lower trunk was estimated using right and left belt markers. Translation of this trunk segment was measured in the anterior-posterior direction, from start of the trial (neutral position) to the point of stability failure. All the subjects were video-recorded from a 45-degree angle. Datavyu software (http://datavyu.org/) was used to characterize postural behavior. The statistical analysis was conducted using SPSS 23 (SPSS, Chicago, Ill.). A two-factor mixed-design ANOVA was conducted with one within factor (Test Session: Pre-Training and Post-training) and one between factor (Group: Experimental and Control). Pairwise comparisons are reported if the interaction was significant and p values were adjusted using Bonferroni's procedure.

Postural behavior variables were not normally distributed, as it was indicated by the non-significant Shapiro-Wilk normality test ($p<0.05$) and visual inspection of Q-Q plots. Therefore, a non-parametric Mann-Whitney U-test was applied to test the potential significant difference between control and experimental subjects in postural behavior during the T stage. The alpha value was set at 0.05 for both statistical procedures.

Figure 17:
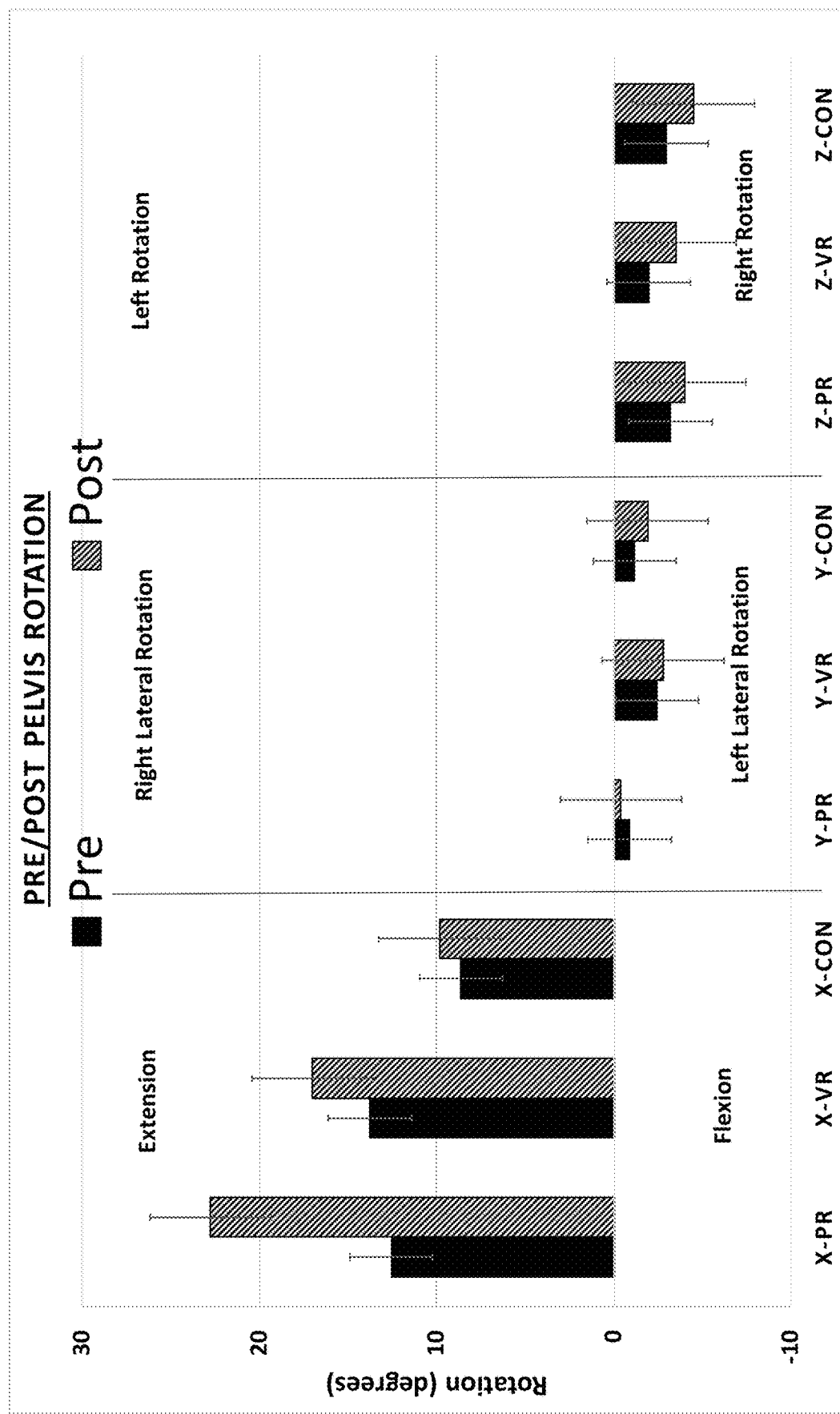
FIG. 17 shows pre and post pelvis rotation relative to the global frame for the experimental and control groups.

The anterior COM lower trunk displacement (e.g. position of belt) during the pre and post-training stages is depicted in FIG. 17. The two groups started from a similar baseline in COM displacement (6.2 cm and 7.0 cm, $p=0.368$). There was a significant Test Session X Group interaction ($F=11.33$ (1.18), $p=0.003$, $\eta^2=0.89$), with the pairwise comparison showing a significant increase of 61.4% in experimental subjects ($p<0.001$) compared to an increase of 14% in the case of controls ($p>0.05$) during the post-training.

Figure 18:
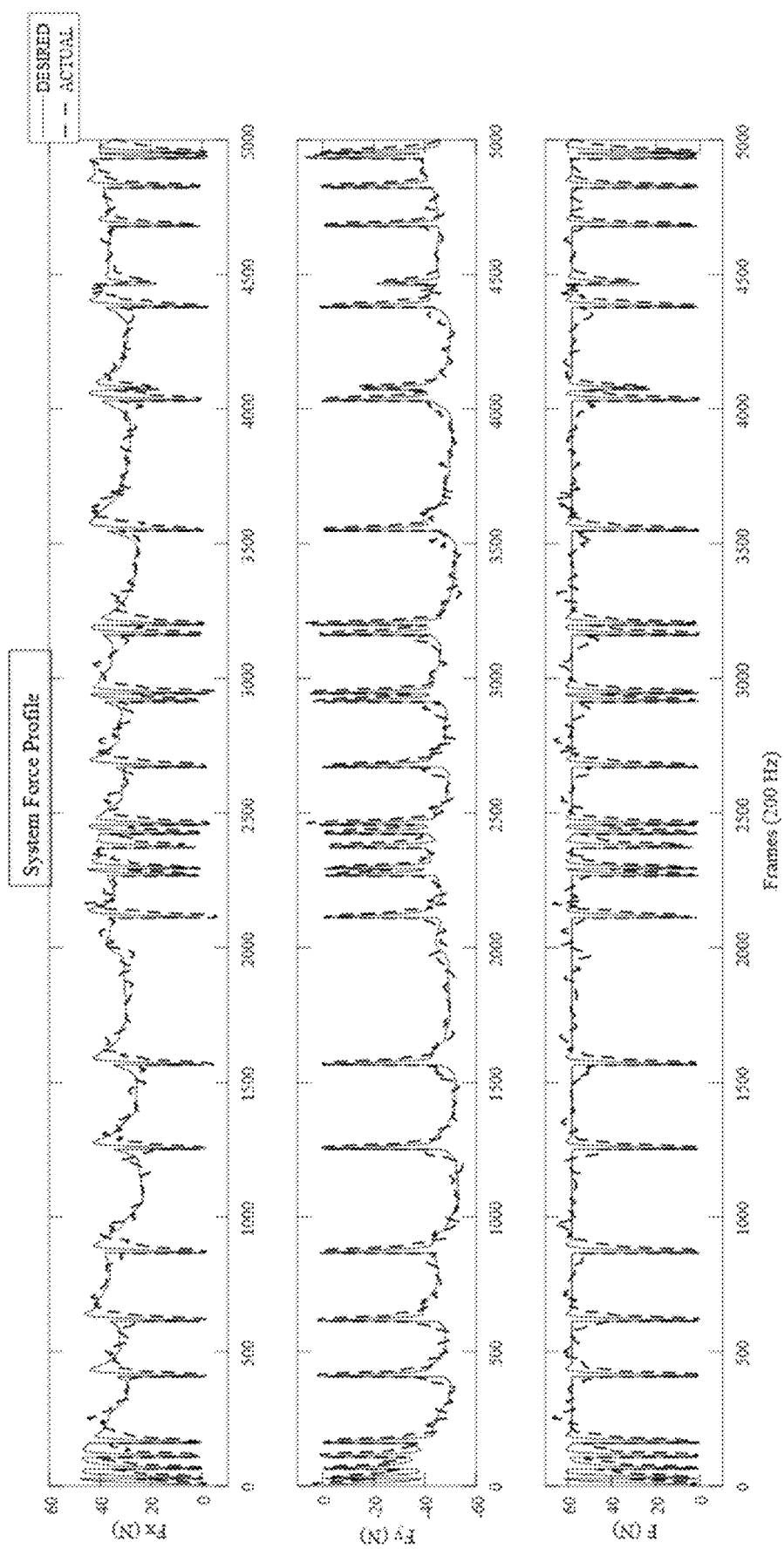
FIG. 18 shows the desired and actual cartiseian force vectors $F_x$, $F_y$, and $F_{resultant}$ to show the ability of the low level controller to achieve the desired trajectory during dynamic movement.
Figure 19:
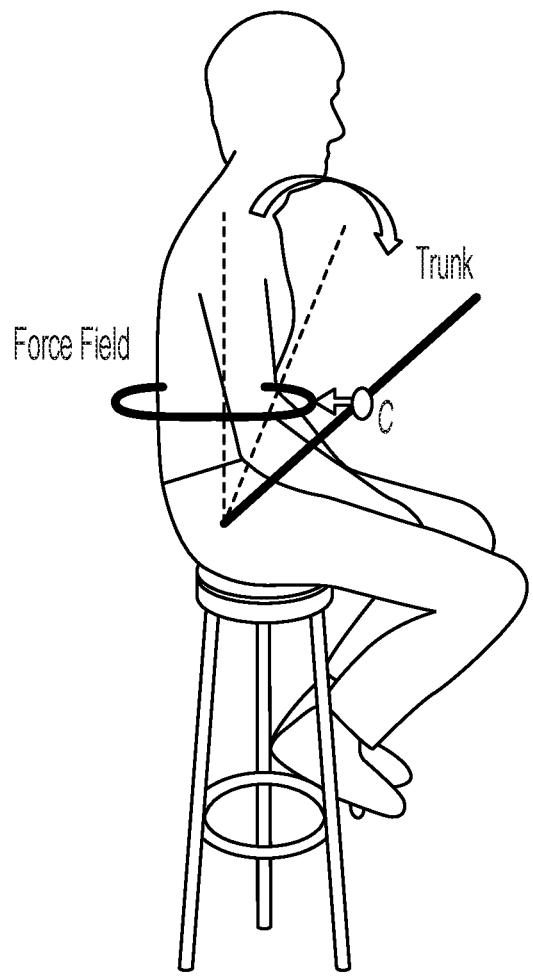
FIG. 19 shows how the matrix A is determined using unit cable length I and direction vector r from the center of the rigid body inside the torso brace, to the cable attachment point on the brace where F is the desired force vector and T is the tension required to achieve F.
Figure 20:
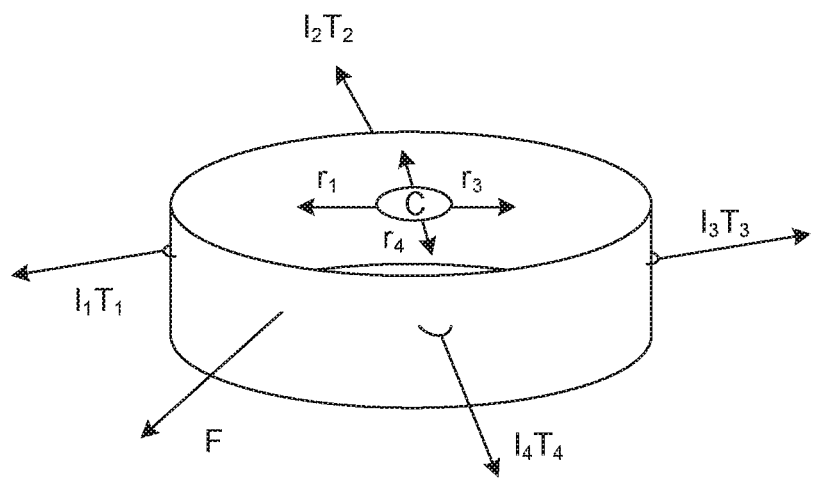
FIG. 20 shows the force assistance to guide the trunk center back to the force field boundary when outside the stability region.
Figure 21:
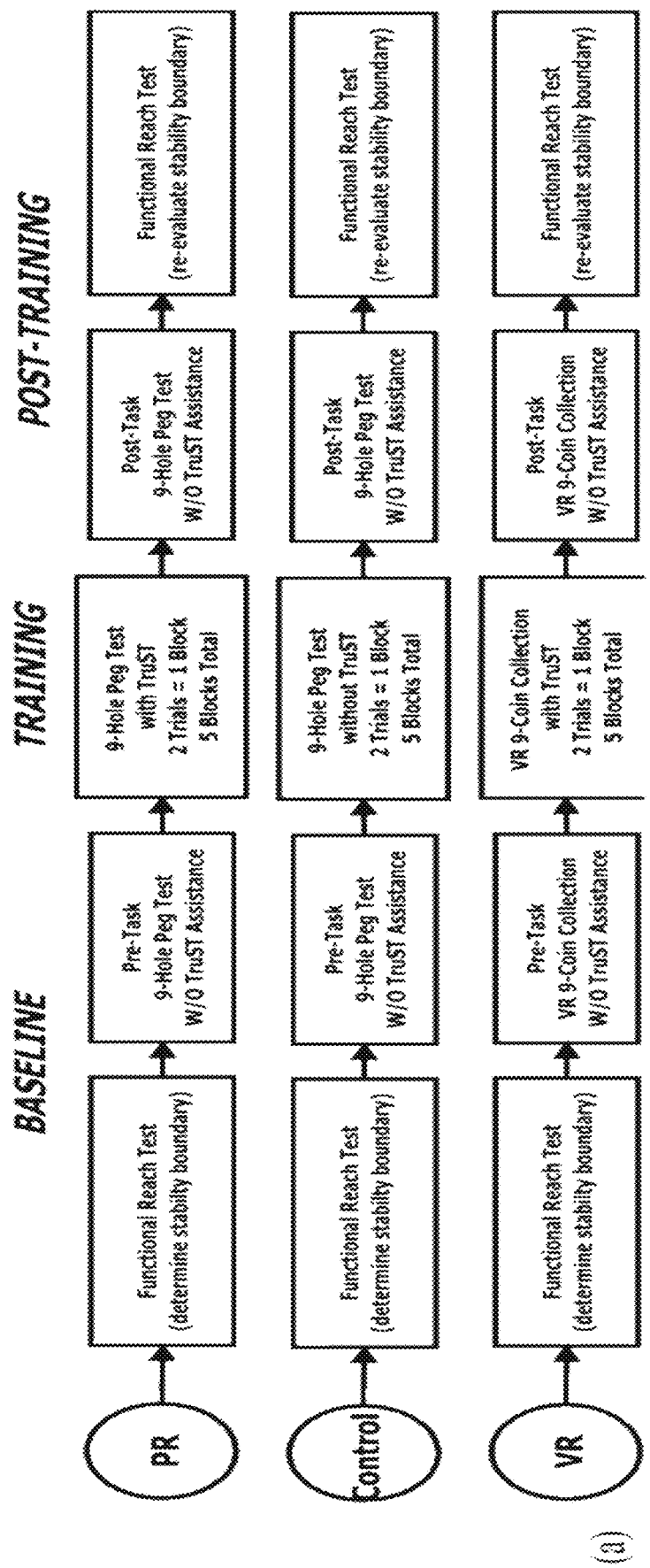
FIG. 21 shows the study protocol for the different study groups.
Figure 22:
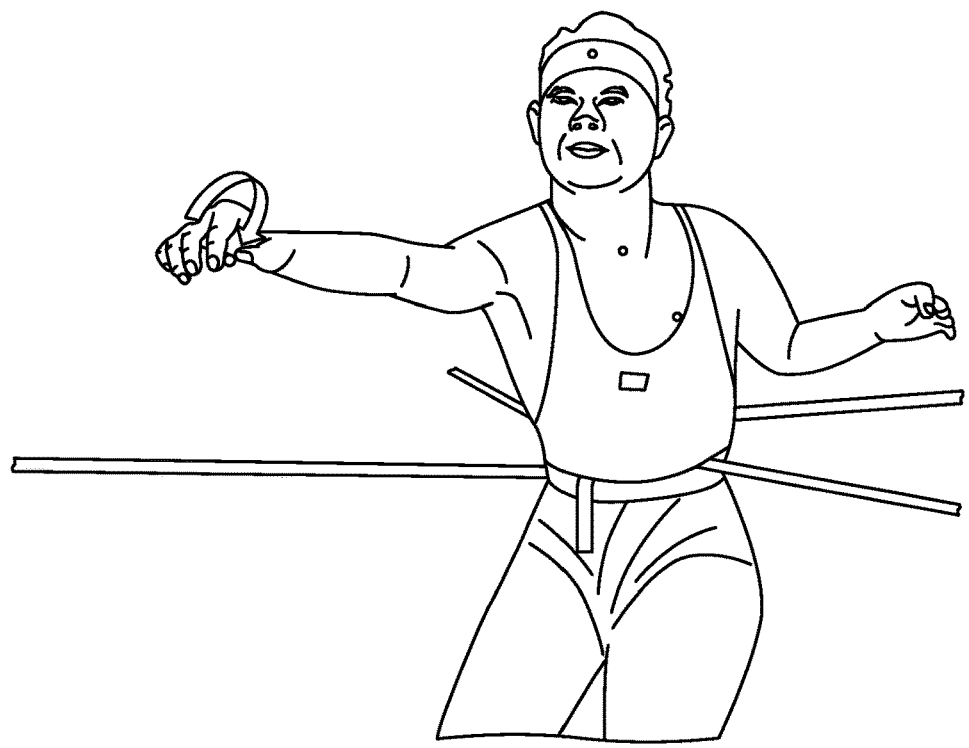
FIG. 22 shows a subject performing a PR nine-hole peg test.

The changes in head, upper trunk, lower trunk, and pelvis rotations are shown in FIGS. 7-11. The pelvis rotation was measured relative to the global frame, while each segment was measured in relation to its caudal segment (e.g. the upper trunk relative to the lower trunk). There was a significant Test Session X Group interaction for lower trunk ($F=5.32(1.18)$, $p=0.033$, $\eta^2=0.59$) and pelvic rotation ($F=8.01(1.18)$, $p=0.011$, $\eta^2=0.76$) in the flexion/extension axes (FIG. 18). These results indicate a significant increase in the rotatory component of both lower thorax (FIG. 21) and pelvis (FIG. 22) only for the experimental subjects that received the training with the TruST. Specifically, after training, lower trunk rotation increased towards flexion by 41.3% ($p=0.028$) and pelvic rotation increased towards extension by 81.0% ($p<0.001$) for the experimental group, while there was no significant change in the control group ($p>0.05$).

The number of reaching or foot placing reactions for postural support was not statistically different between the experimental and control groups ($U=26.5$, $p=0.06$). Nonetheless, controls (Mdn: 4, Min: 1, Max: 22) showed significantly greater number of hand contacts with the table for either postural support or recovering verticality ($U=23.5$, $p=0.04$) compared to experimental subjects (Mdn: 2, Min: 0, Max: 8). Note TruST was active and providing force assistance, on average, 97% of the total time of the seated reaching training across the 5 blocks of trials in the experimental group.

In this proof-of-concept study, it was experimentally determined if specific practice of a seated reaching task at and beyond the individual's point of postural stability failure, without foot support, could enhance volitional control of upper body and further the stability limits established by the configuration of the pelvis. Experimental results demonstrated that over a single training session, on average, the subjects were able to significantly translate their body further anteriorly from their neutral postural configuration and significantly increase the rotational profiles of the lower trunk and pelvic segments in the flexion-extension plane of motion following the assist-as-needed force training with the TruST. Additionally, the subjects of the experimental group did not require frequent and long-lasting hand contact with the table during the training phase.

As was seen with the control group, it was difficult for subjects to train at the border of stability failure without any external assistive forces. As subjects completed each trial of the nine-hole peg test, it was difficult for them to maintain dynamic postural stability with the motion of the arm during the reaching task at or beyond their stability boundaries without using their hand or wrist for support on the peg board. It is possible that without assistive forces, individuals often fail at their stability limits and are not able to explore a larger range of motion and a stable postural configuration required to maintain or recover seated balance while actively reaching to insert and remove the pegs. Therefore, the sensorimotor postural experience required for adjusting their postural kinematics to complete the task successfully may be diminished compared to the experimental group who were provided with the assist-as-needed force from TruST. It was seen that the experimental group spent on average 97% of their training task performance utilizing the assistive forces. This exploratory outcome suggests that reaching further past the maximum arm's extension and at and beyond the individual's point of postural failure requires continuous volitional shifting of the lower trunk to avoid falling or using hands for body support.

Nikolai Bernstein's theory of motor learning states that the central nervous system's (CNS) hierarchy of control mechanisms for posture and movement are organized with distributed and parallel processing. Neural mechanisms that integrate posture with dexterity movements (e.g. reaching control) are distributed in the CNS and are recruited in patterns that are task and context dependent. The manner in which the CNS recruits the DOF depends on the variables it uses to plan, time, and control the movement. By providing an assistive force at an individual's point of postural stability failure, the subjects experienced larger upper body displacements with the subsequent selective training in the control of key segments for maintaining postural stability during the reaching task practice. These segments were lower trunk and pelvis. The results demonstrate that the control group was not able to enhance the degree of selective rotations of the lower segments (lumbar and pelvis) and these remain similar before and after the training. The movement of these lower segments followed an 'in-block' mode of control, in which the DOF of these key segments are constrained during the linear translation of the upper body during the functional reach task at and beyond the postural limits. However, in the case of the experimental group, the subjects were able to release the lower thorax and pelvic DOF and exploit their rotational amplitude in the flexion-extension plane of motion after providing the assist-as-needed force control with the TruST. Thus, subjects in the experimental group were able to experience and control a set of postural kinematics that would have been impossible to undergo without the selective force field provided by the TruST.

The overall goal of this assist-as-needed control strategy via the robotic device TruST is to train subjects in an accurate reaching task beyond maximum arm extensions and at/beyond their point of postural stability failure. With TruST, the volitional neuromuscular control of lower thorax and pelvis is continuous, allowing them to actively participate in the postural learning process required to attain this specific reaching task context. The effect of training and lack of subject-TruST inter-dependence is observed because the assistive force was progressively reduced across the five blocks of practice. In addition to this, the TruST was inactive during the post-assessment and yet significant improvements were observed for the translational and rotational components in the voluntary control of seated posture beyond the point of stability failure.

The application of this device in combination with motor learning and control principles can be seen as potentially beneficial for use in patients with neurological or musculoskeletal disorders, such as in Cerebral Palsy or Spinal Cord Injury. In these pathological conditions, patients have little or no voluntary seated postural stability in both static and dynamic dimensions of control.

Other possible factors exist such as the level of fatigability of the paravertebral muscles, which could be reduced in experimental subjects compared to controls. Some of the technical limitations of this study may include the ability to distinguish between the changes in muscle activation, joint torques, and kinematics that lead to increased postural stability beyond the point of failure. Although posture is a combination of several intricate biomechanical processes, it would be beneficial to include these parameters in future experiments in order to identify which parameters are likely to play a larger role for adapting a more stable posture.

An embodiment of an active posture training device, TruST is described. Benefits of training subjects at and beyond their point of stability failure are shown for enhancing their maximum volitional control in seated trunk displacement with and without assist-as-needed forces. Postural stability is defined as the ability to displace the estimated COM of the lower trunk segment further from the neutral postural configuration of reference without postural collapse of the upper body. The results demonstrate that the force field concept used in TruST has potential benefits in the rehabilitation of posture. Training with assistive forces at a person's point of postural stability failure can increase the rotational amplitude of pelvis and lower thorax in order to displace the upper body under volitional control further away from the center of the pelvic configuration. These outcomes are in accordance with: (a) the principle of practice specificity in motor learning when providing appropriate assistive forces with the TruST and (b) Bernstein's theory of motor learning, where the CNS can recruit and release the DOF to organize postural kinematics to attain the goal of reaching within and beyond the individual's point of stability failure.

The following describes further work on a VR type of system and methods.

VR offers a three dimensional user interface along with real-time computer simulation of an interactive environment. It can present complex multimodal sensory information to the user and can elicit the feeling of realness and engagement. The capability of VR can potentially offer many advantages in rehabilitation. Although physical reality (PR) training is the traditional and proven method towards rehabilitation, the successful integration of VR can allow access to unexplored rehab paradigms, and provide a quantitative and qualitative comparison of VR and PR based methods.

An advantage of VR over PR training activities of daily living (ADL) during rehabilitation is the added layer of cognitive engagement due to gaming aspect. With specific gaming scenarios that require a specific movement, VR based systems can allow exploration of how the brain controls movement, learns new movements, and relearns movement skills after an injury. VR also provides the ability to vary a training task in a small space, without having to physically alter the environment. Being able to train on a variety of different tasks can provide a better overall improvement in function than repetition of the same task. Specifically, VR has potential in rehabilitation of patients with neurological deficits, where the cost of treatment is high, therapist time is limited, and repetitive training is shown to produce positive outcomes. The use of VR systems, integrated with novel robotics, paves the way for testing a larger range of patient training paradigms and enhancing scientific exploration. In return, use of such systems can reduce the cost of rehabilitation, allow therapists to be more productive in their training, and allow extended duration of rehabilitation. VR can serve as a tool for sensory stimulation for neural and functional recovery by providing movement observation, imagery, repetitive massed practice, and imitation therapy.

Research also supports "task oriented training" for rehabilitation, where the motions relevant to a certain activity of daily living are part of the rehab training. Studies have shown that quantity, duration, and intensity are important variables in learning and relearning motor skills and in changing neural architectures. Evidence demonstrates that plasticity is use dependent and intensive massed and repeated practice may be necessary to modify neural organization. Using VR and robotics, various areas of motor rehabilitation can be studied. One such area is seated postural control. Seated postural control requires the stabilization and control of the head and trunk to complete many daily tasks, e.g., reaching for an object beyond maximum arm's length. Although sitting statically upright can be less demanding with the center of mass (COM) of the upper body centered over the base of support (BOS), large and quick displacements of the upper body outside the pelvic boundaries can cause a sudden shift of the COM away from the center of the BOS, creating a lack of a stable neutral upper body and pelvic position. In this situation, a precise control of the upper body is required to recover verticality and maintain stability.

Although healthy individuals can perform complex leaning, reaching, and grasping tasks readily, patient populations with neurological or musculoskeletal dysfunction can present control deficits during shifting of their weight and moving their upper body within and beyond the pelvic boundaries in the seated position without losing stability and balance. These tasks are neurologically demanding requiring the primary motor cortex, somatosensory systems, and frontal and parietal areas to play an essential role to maintain balance. Therefore, there needs to be a coordination between the fine motor circuitry and musculoskeletal postural framework. The postural control function consists of generation of direction specific kinematic movements and adaptation of these specific movements on the basis of multi-sensorial afferent inputs. Studies have shown that direction specificity emerges as a result of self-organization of intersegmental components during exposure to new positions. Therefore, performing and exploring a new or more difficult task can show task-specific kinematic adaptations of posture.

In rehabilitation of patients with severe motor dysfunction, postural training is usually conducted by fixing the trunk or pelvis using a rigid frame, strap, or cord. Though this can provide added stability while practicing a task, this method is passive and restrictive, limiting the patient's postural adjustments to be at the level of the trunk that is held fixed and reducing postural sensorimotor experience due to the constraint of the trunk's degree-of-freedom (DOF). A VR environment corresponds with a PR environment, and synchronized it with the TruST to compare the benefits of postural training using VR with TruST to PR with TruST and PR without TruST assistance (control group). TruST is a cable-driven robotic platform that can be used to: (a) apply assistive or resistive forces-moments at a segment of the trunk, (b) provide multi-directional perturbations, and (c) provide a force-tunnel to support at an individual's boundary of instability. In addition, assistive forces provide error-based haptic feedback for proprioceptive training. The TruST allows for self-control of postural adjustments during training.

The use of VR-based training tasks with TruST has been demonstrated for improving volitional trunk displacement for direction specific kinematic adaptation. Training activities may consist of novel challenging postural tasks conducted without foot support, to challenge postural balance and coordination. Ten healthy adult subjects were trained at their maximum trunk displacement, or failure point, in a VR environment and then compare with results in a real environment with physical objects with and without the assist-as-needed forces of the TruST. A motion capture system was used to determine the subject's maximum seated lower trunk COM displacement and a force tunnel was created at that distance. During the experiment, subjects performed a total of five blocks of two trials each. For PR, this consisted of a nine-hole peg test placed at the subject's point of stability failure, measured during the baseline stage, while for VR, this consisted of a virtual nine-coin collection with coins placed at the same measured point of stability failure. The study tests and supports the hypothesis that a single training session in a VR environment, at a maximum stability region, increases lower trunk COM displacement and shows no significant difference to training in a real environment with physical object manipulation.

The TruST uses four cables connected to each corner of a torso belt to apply the desired force/moment in the transverse plane. If the desired force-moment vector at the belt/trunk segment is represented by $F \in R^{6 \times 1}$, then the desired tensions in the cables to achieve F for a four-cable system, $T \in R^{4 \times 1}$, can be obtained by solving the following expression for T, while satisfying all auxiliary constraints.

$$F = AT \qquad (1)$$

where, $$F = [F_x F_y F_z M_x M_y M_z]^T \qquad (2)$$

and A is a 6×4 structure matrix based on the system geometry, where six is the degrees of freedom of the end effector and four is the number of actuated cables. The matrix A can be expressed as:

$$A = \begin{bmatrix} \cdots & \vec{T}_i & \cdots \\ \cdots & r_i \times \vec{t}_i & \cdots \end{bmatrix}_{6 \times 4} \qquad (3)$$

where $\vec{T}_i$ is the $i^{th}$ unit cable length vector away from the rigid body and $r_i$ is the vector from the center of the rigid body to the cable attachment point i on the rigid body (FIG. 2A).

The desired transverse planar forces, $F_x$ and $F_y$, are computed by the force-tunnel controller (discussed in next section), while inequality constraints were set to create an upper and lower bound for $F_z$, $M_x$, $M_y$, and $M_z$ which allow the solver to solve Eq. (1) for tension values (T) within the inequality constraints.

The function of the force is to apply a specific F, on the trunk, at the level of the torso brace. Cable systems require at least n+1 cables to generate a n×1 F vector, for n degrees of freedom (DOF). Since active control is required of only two DOF ($F_x$ and $F_y$), with four cables we have an under-determined system with infinite solutions for T within the inequality constraints. For this reason, we require a quadratic solver with an objective function to find the minimum normal solution for tension values.

As seen with linear programming, for T≥0, the optimal solution is found at the corner of a convex hull of the feasible set. To minimize discontinuities for positive T values, a quadratic programming based optimization scheme was implemented to solve Eq. (1) for T The objective function minimizes deviations between T (current tension) and $T_p$ (the tension values at the previous time instance) to allow for a smooth continuity in cable tensions, as seen in the literature on cable robotics, and is defined as follows.

$$\min f(T) = \frac{1}{2}(T - T_p)^T (T - T_p) \qquad (3)$$

The high level controller consists of a force tunnel controller which creates a virtual force field at a specified radius around the subject's trunk in the transverse plane. The center of the lower trunk is obtained by using a motion capture system and computing the estimated centroid of the left and right lateral points on the belt. As seen in FIGS. 2B and 3, the controller is designed such that when the trunk center C, defined by the belt, is outside a specified circle of radius r, a normal planar force F is applied to assist the trunk towards the force field boundary. Details on the calculations can be found in.

The low-level controller runs at 1 k Hz using LabVIEW PXI real time controller. To achieve a desired tension, a specific current is provided to the motors. This is relative to a voltage calculated using a pre-measured motor constant relating voltage and tension, an open loop feed forward term and a closed loop PID based feedback term, as described in A VR gaming environment was created in Unity3D, synchronized with Vicon motion capture cameras, and projected in a three-dimensional form inside an Oculus Rift headset. The VR gaming environment consists of a drone and a coin collecting gaming task. Coin location is specified by user input based on the maximum reach measured during baseline. The drone is controlled by hand motion to provide a virtual representation of the subject's hand position. The global XYZ coordinate of the hand is captured in real time through Vicon and sent to the VR environment via User Datagram Protocol (UDP) programmed in the main controller, to ensure that the tracking of the hand and placement of the coin in VR were correctly correlated with PR. The inertial frame of the Vicon and Unity3D were calibrated to represent the middle of the TruST device. Using this calibration, we were able to transform real world measurements accurately into the game platform units. To improve depth perception and enhance the 3D effect, we placed virtual props, such as street lamps and canisters, in the environment. See FIG. 11.

Figure 23:
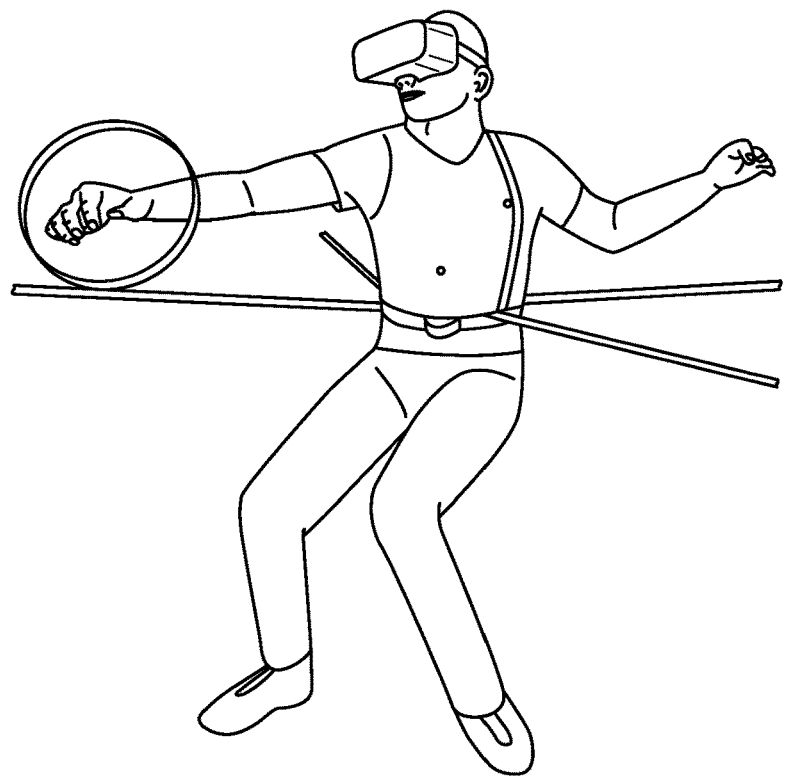
FIG. 23 shows a subject performing a VR task (nine coin collection).

Ten healthy adult subjects were recruited for the VR training group. They were compared to 20 healthy adult subjects, who were randomly assigned to either the physical environment/reality training (PR) or control group (PR with no TruST support). The VR group consisted of seven males and three females (Avg: 25.7 yrs/155 lbs/174 cm, 9 right-handed and 1 left-handed). The PR and control group consisted of 12 males and eight females (20-30 yrs, 19 right-handed and 1 left-handed). The training protocol was approved by Columbia University's institutional review board and consisted of three stages: baseline (BL/pre-training), training (T), and post-training (PT), as outlined in FIG. 21. Before training, subjects were instructed about the training protocol. The PR and control groups were randomly assigned and were not told which group they were in. The VR group was aware of their group as they had to wear a VR headset. Retro-reflective markers were placed on the subjects to record kinematics using a Vicon motion capture system. The subjects were seated on a stool at the center of the TruST. An adaptable but rigid three-inch wide belt was attached to the lower trunk (lumbar) region. The training activities were separated as PR training using a nine-hole peg task (FIG. 22) or VR training using a virtual coin collecting game task (FIGS. 23 & 24) structured in the same format (collecting nine coins spaced out at the same distance as the peg board). The peg board had 3×3 holes of 4 mm diameter spaced at 5 cm apart, and the subjects were instructed to pick a peg from their dominant side and place it into the peg board. For the VR group, to simulate the same training in a virtual environment, the subjects were instructed to touch a button on their dominant side before collecting the coins spaced in a 3×3 configuration at 5 cm apart (FIG. 11).

Figure 24:
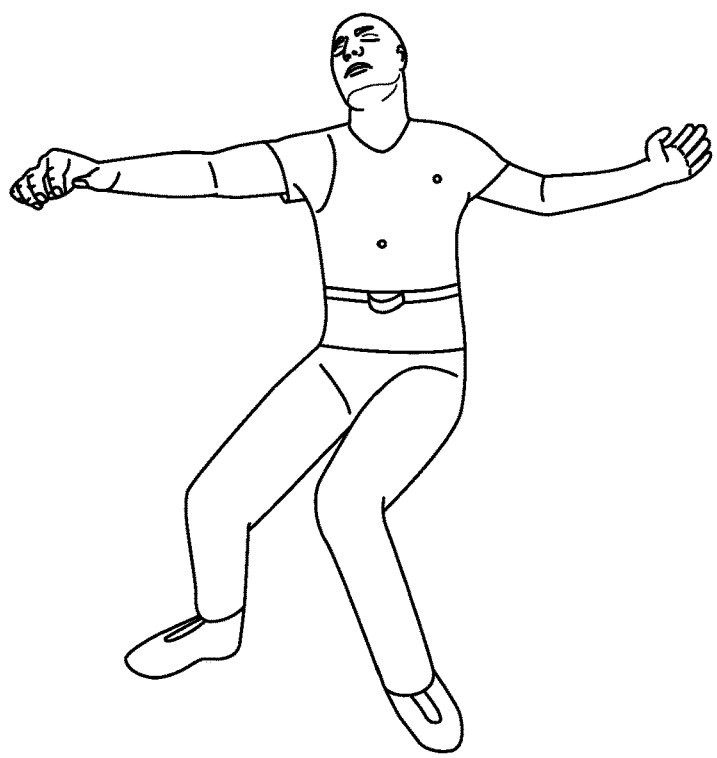
FIG. 24 shows a subject performing PR reach task to define region of stability and boundary of force field.
Figure 25:
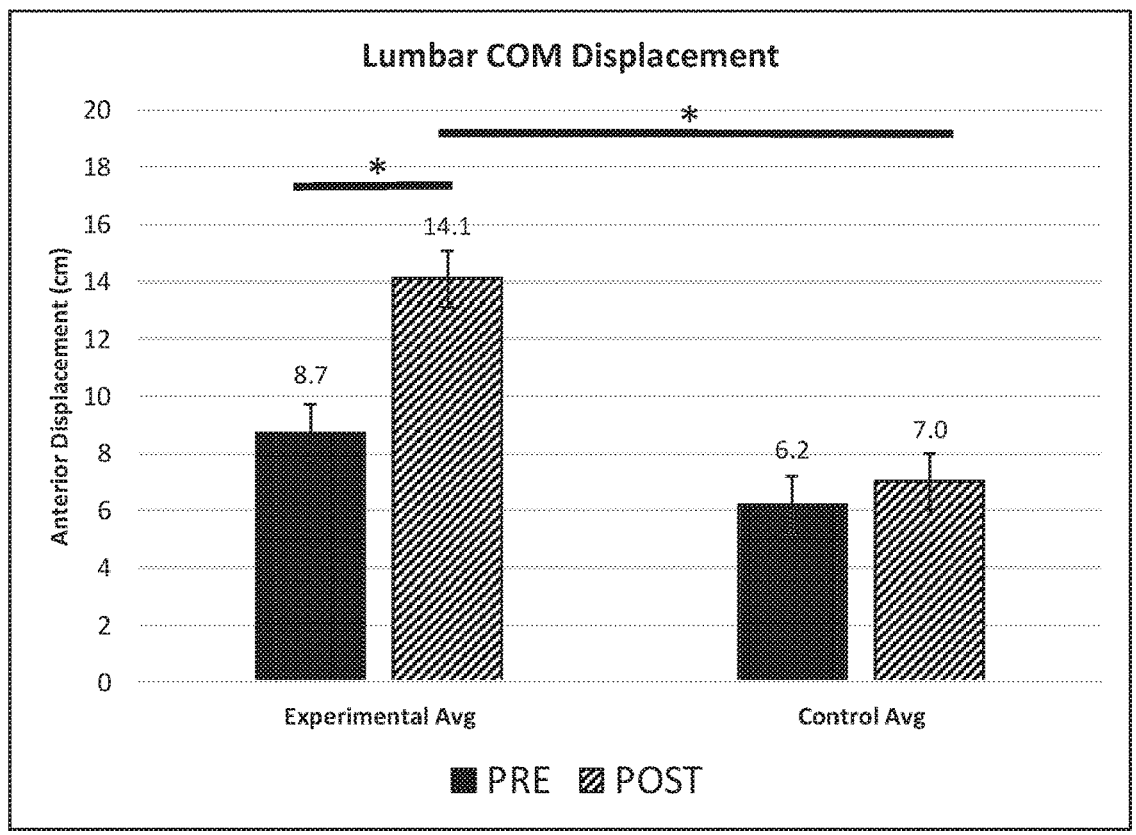
FIG. 25 shows lower trunk COM displacement measured from the stable/neutral position to the failure point during the functional reaching task, pre and post training for the PR, VR, and control group (*=p<0.005).
Figure 26:
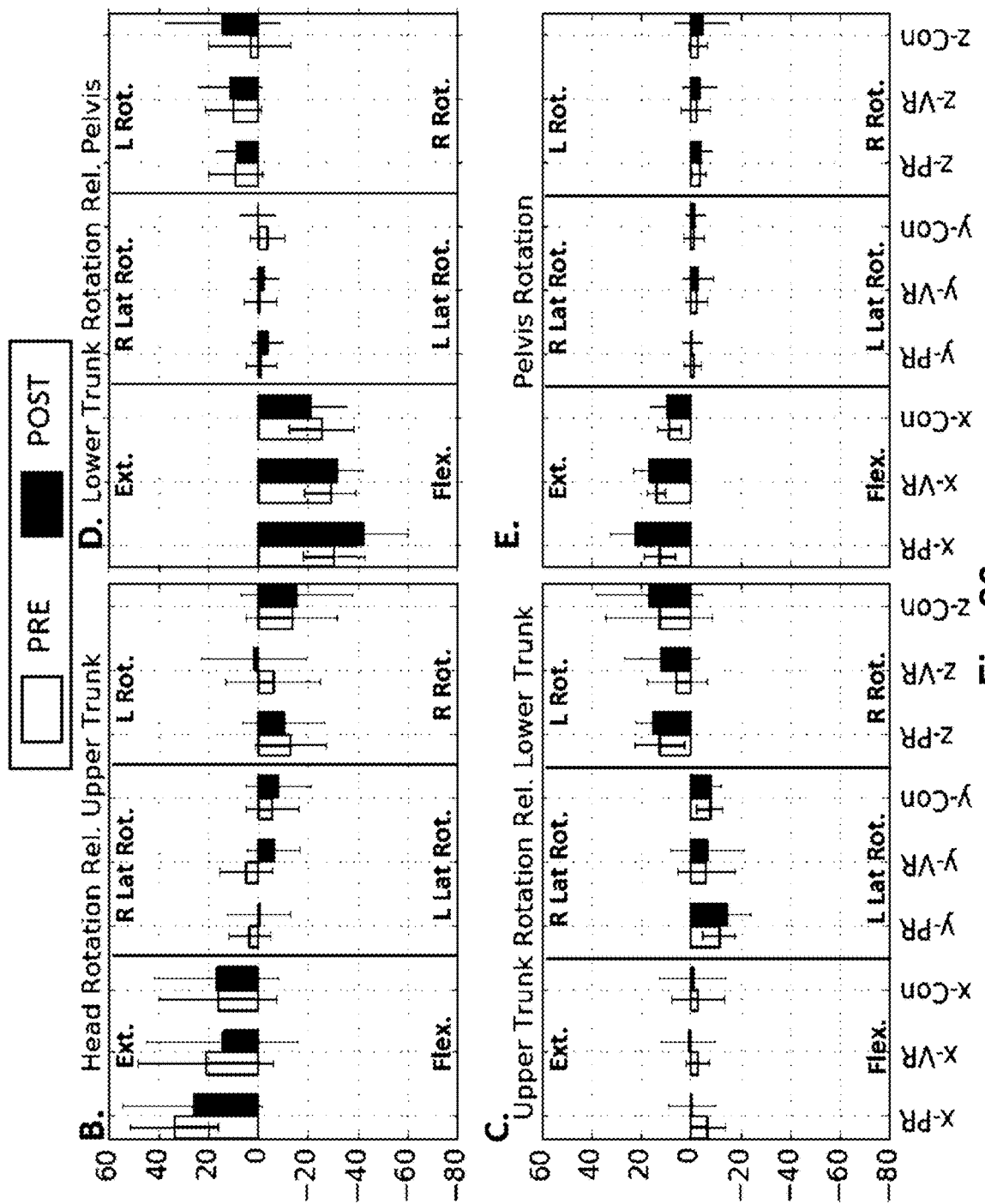
FIG. 26 shows results of pre/post segmental rotations during a modified functional reach test across multiple groups.

During the BL, the pre-training tasks consisted of the functional reach test to determine the maximum lower trunk displacement and define the point of stability failure for all three groups (FIG. 24). The PR and control groups conducted a pre-training nine-hole peg task without assistive forces, while the VR group conducted the virtual coin collecting game task with no assistive force. During the training stage, five blocks of two consecutive trials of the nine-hole peg task was conducted for the PR and control groups, while the VR group performed the virtual coin collecting game task. This was followed by PT stage in which the PR and control groups performed the functional reach and nine-hole peg tasks, and the VR group performed the functional reach and coin collecting task. These PT tasks were for re-assessment of postural kinematics without external assistance from TruST.

The function of an assist-as-needed force strategy is to minimize subject dependency on assistive forces and to motivate self-initiation and self-correction of postural kinematics. With the force field control, the subject is not administered any supportive forces within their measured stability region, as this is their pre-intervention workspace. As the subject is challenged to tasks outside their stability boundary, the assistive forces are triggered to support the posture and allow adequate time to explore further areas outside of their stability boundary. The haptic feedback provided through the assistive forces notifies the subject of their proximity to their stability boundary. As the subjects experience this new workspace and realize their ability to maintain stability, they are naturally encouraged to explore new postural configurations to successfully occupy the new workspace. In contrast to physical therapy based interventions for postural training, our protocol was designed to provide minimal required assistance, determined through system testing, to assist subjects during training tasks described in the following sections.

During the experiment, all subjects were asked to sit on a flat, wooden stool. The torso belt was firmly placed at the lower trunk. The subjects were asked not to use any foot or hand support while performing the functional reach task and the nine-hole peg task. However, they were allowed to move their body freely as desired, to complete all tasks to the best of their ability. All tasks started from a stable neutral position with the head and trunk centered over the pelvis, with elbows in external rotation and bent 90-degrees in the air. Subjects were instructed to perform each task as fast and accurately as possible, while maintaining postural control. During training, subjects were allowed to use a finger or the volar area of the wrist for support on the table, only if posture stability was lost during the placement of the pegs.

For the functional reach test, the subjects were asked to displace a wooden block anteriorly as far as they could in a controlled and self-paced manner. If the subject used any support or lost balance, the task was stopped and the point of stability failure was kinematically recorded. If the subject lost balance prematurely, they were allowed to repeat the task. We defined premature loss of balance if 1) the subject touched the table surface for support, or 2) there was premature foot-ground contact for displacing the piece of wood at further distance.

The reach test was performed at BL and PT, with the shoulders flexed at 90-degrees and arm parallel to the floor. The failure point was used to identify the boundary of postural stability. This boundary specified the maximum anterior translation of the lower trunk before postural collapse. This maximum anterior translation was set as the radius of the force field circle, allowing for the TruST device to provide assistive forces when outside this radius.

For the PR and control groups, the nine-hole peg board was then placed in front of the subject. The furthest row of the board was positioned in line with the position of the wooden block where the stability failure happened during BL. For the VR group, the coin position was set to the wooden block position, or the stability failure point. The subjects were instructed to grab a peg from their dominant arm and place it onto the board from the dominant side to opposite side, working from the closest row to the furthest. For VR group, the subjects were instructed to touch a button at their dominant side and then reach to grab the coins, as these appeared one at a time in a specific order, from the dominant to the opposite side and from the closest to furthest away.

The coins also ranged in color from bronze, silver, and gold, to identify from closest to furthest in distance. After inserting the nine pegs, subjects removed these in the same order, while the VR group recollected the coins in the same order. A complete cycle of inserting and removing pegs or collecting coins twice was identified as a single trial. Two consecutive trials conducted at a time were defined as a block. Five blocks were conducted, with the assist-as-needed, error based force for the VR and PR groups at or beyond the predefined maximum lower trunk displacements (e.g. point of stability failure). Accordingly, the subjects moved independent of any assistance as long as they were inside the force tunnel but received assistance at and beyond their failure point. The assistive force was decreased by 2N (3.33%) linearly after each block of training, starting from 60N, determined through system testing. The subjects were allowed as much rest time as they needed between sessions to a maximum of five minutes. The same protocol with the peg board was followed for the control group but no assistive forces were provided.

The data were analyzed to assess the spatiotemporal changes in head, upper trunk, lower trunk, and pelvis translation and rotation between pre and post functional reach test between the VR, experimental, and control group. The data were analyzed using MATLAB (MathWorks, Natick). The COM of the lower trunk was estimated using right and left belt markers. Translation of this trunk segment was measured in the anterior-posterior direction, from start of the trial (neutral position) to the point of stability failure. The statistical analysis was conducted using SPSS 23 (SPSS, Chicago, Ill.). We conducted a two-factor mixed-design ANOVA with one within factor (Two Groups: Pre-Training and Post-Training) and one between factor (Three Groups: VR, PR, Control). Pairwise comparisons are reported if the interaction was significant and p values were adjusted using Bonferroni's procedure. The alpha value was set at 0.05 for both statistical procedures.

The anterior COM lower trunk displacement (e.g. position of belt) during the pre and post-training stages is depicted in FIG. 6. There was a significant Test Session X Group interaction ($F=4.47(2,27)$, $p=0.021$, $\eta^2=0.72$), with the pairwise comparison showing a significant increase of 61.4% in the PR group ($p<0.001$) and 34.4% in VR group ($p=0.004$) compared to an increase of 14% in the case of controls ($p>0.05$) during the post-training. Both PR and VR showed significantly more range of motion in translation compared to the control, 515% ($p=0.001$) and 278% ($p=0.006$) respectively, while there was no significant difference between the PR and VR group ($p>0.05$).

The changes in head, upper trunk, lower trunk, and pelvis rotations are shown in FIGS. 7A-7E. The pelvis rotation was measured relative to the global frame, while each segment was measured in relation to its caudal segment (e.g. the upper trunk relative to the lower trunk). There was a significant Test Session X Group interaction for lower trunk ($F=3.41(2,27)$, $p=0.048$, $\eta^2=0.59$) and pelvic rotation ($F=5.37(2,27)$, $p=0.011$, $\eta^2=0.80$) in the flexion/extension axes (FIG. 7). These results indicate a significant increase in the rotatory component of both lower thorax (FIG. 10) and pelvic rotation (FIG. 11) for the PR group compared to the control, with a tendency of interaction effect for pelvic rotation ($p=0.056$) between the VR and control group.

Specifically, after training, lower trunk rotation increased towards flexion by 41.3% ($p<0.001$), while pelvic rotation increased towards extension by 81.0% ($p<0.001$) for the PR group. However, the VR group showed an increase toward flexion by 10.5% ($p=0.516$) and a pelvic rotation increase towards extension by 23.5% ($p=0.123$). There was no significant change in the control group ($p>0.05$) and no interaction effect between the PR and VR group.

In this proof-of-concept study, we tested if specific practice of a seated reaching task (without foot support) in a virtual environment, at and beyond the individual's point of postural stability failure, could enhance volitional control of upper body and extend the stability limits established by the configuration of the pelvis. We compared the results with experiments conducted in a real environment with physical object manipulation (PR) and with a control group to extract the advantages of a VR based training. Experimental results demonstrated that on average, over a single training session, the subjects were able to significantly translate their body further anteriorly from their neutral postural configuration with both physical reality and virtual reality training with TruST. Physical reality training also significantly increased the rotational profiles of the lower trunk and pelvic segments in the flexion-extension plane of motion. On the other hand, the control group (physical reality training without assist-as-needed forces) did not show any significant change.

The significant increase in anterior lower trunk translation seen with the PR and VR groups, but not with the control group demonstrates that the TruST robotic system has a significant beneficial effect in seated posture training. The assist-as-needed force strategy allows the subjects to train at their maximum stability limits without failing. This allows the subjects to explore a larger range of motion and a stable postural configuration required to maintain or recover seated balance. On the other hand, the control group does not get enough time to spend at the stability boundary without failing and thus has to use their hand for support. As a result, the sensorimotor postural experience required for adjusting their postural kinematics to complete the task successfully may be decreased compared to the PR and VR group who were provided with the assist-as-needed force from TruST. Furthermore, it was visually apparent that the control group had difficulty maintaining dynamic postural stability during the peg board test at positions beyond their stability limits. In this case, the subjects repetitively had to place their fingers for support while the PR group showed more consistency in their reaching, without often using the hand for support. Accordingly, the VR group did not have a table for support, as the experiments were virtual, and rarely placed their hands on the stool to regain stability during training.

In comparing the PR and VR groups, to observe the difference between training requiring physical object manipulation or through a gaming experience, it was seen that the PR based training produced slightly better outcomes. Although both PR and VR groups showed significant increases in lower trunk translation, only the PR group showed significant increases in lower trunk and pelvic rotational profiles, while the VR group showed non-significant increases. The training effect with the TruST showed that the pelvis increased towards extension while the lower trunk increased towards flexion, but only the changes in the PR group were significant. This suggests that although both PR and VR training showed significant increases in postural range of motion, PR training can potentially show better outcomes. Yet, there were no significant differences in results between PR and VR. It was also noted that in VR, there was a tendency for an interaction effect for pelvic rotation (p=0.056). This can mean that with a larger sample size, VR could also show significant improvements in rotational profiles. Since there was no difference in statistical significance between PR and VR, we cannot specifically conclude that one is better than the other, yet both individually showed improvements in postural kinematics. As discussed in, Nikolai Bernstein's theory of motor learning states that the central nervous system's hierarchy of control mechanisms for posture and movement are organized with distributed and parallel processing, where neural mechanisms that integrate posture with dexterity movements (e.g., reaching control) are recruited in patterns that are task oriented. By providing an assistive force at an individual's point of postural stability failure, the subjects experienced larger upper body displacements, and were better able to integrate the postural requirements within the context of the specified task. As the task was practiced at the point of stability failure or maximum level of stability, the subjects were better able to control each segment separately, thus increased their range of motion.

The purpose of this study was to assess the improvements in seated postural range of motion with the use of an assist-as-needed force strategy from TruST, in a virtual and real training environment. For this reason, the virtual gaming experience was made to be less variable, and more repetitive in nature to mimic the training provided by a nine-hole peg test. Although controlling a drone and collecting coins add a gaming experience, the task can be seen as repetitive where a user can master the motion and timing required to successfully complete the training. For this reason, the level of cognitive engagement desired for a game based training may be diminished, leading to fewer improvements in outcomes as seen with the rotational profiles for the VR group. On the other hand, physical training such as the peg board, require adequately completing and witnessing an outcome (e.g. peg going into a hole) that feeds on visual and tactile stimulus, which might have led to an increased range of translational and rotational motion.

The main advantage that a VR can provide is variability of training. With variation of training, the cognitive demands and engagement are increased, as the user is required to make decisions under time constraints and possibly rewarded for improving through a scoring system. It maybe that due to a lack of variability in the training task in the VR group, the outcomes were not as large as those seen with the PR group. Yet, there was no significant interaction or difference between the PR and VR groups.

Even though the improvements are significant only in translation and not in rotation, VR training can be appreciated for its trade-offs. Although physical training would suggest a better outcome, VR training could be performed more readily without the need for added personnel, be more cost effective, and be extended to higher variability in training and in a low-cost environment, while physical (PR) training requires specific hardware and personnel for training. VR training can also be conducted at home and therefore can be done more often than PR training. It may be that more sessions of training can show far better improvements than a more challenging training conducted with fewer sessions. Another advantage of VR is that we can create direction specific, task-oriented trajectories for training and modify the training task according to the subject's spatial position, recorded by a motion capture system. By using a virtual environment, we can adapt the difficulty of the training sessions progressively, challenging the subject and increasing the cognitive demand to complete the task successfully. This can be tested in future studies.

The disclosure shows, by direct comparison of similar tasks, that VR training can improve postural range of motion when used with TruST. With the adherent similarity between VR and PR towards postural improvements, we are inclined to believe that the ease of conducting training and the low cost make VR an excellent source of providing rehab training. In areas such as rehab of children with musculoskeletal disorders, this may be an optimal way to incorporate rehab in their daily lives, along with school and homework, where the remaining time between PT visits and leisure time is limited, by combining the two together. It may be that with increased normalcy in daily schedules and decreased mental fatigue towards PT visits, children patients may show improved outcomes. We are raising questions for future investigation through this work, where positive rehab outcomes may not only be a factor of training but also the normalcy in lifestyle and the feeling of compromise between rehab and leisure time. Seeing preliminary benefits from VR, we believe that VR based rehab might show improvements in rehab outcomes, due to not only to the primary intervention, but the secondary factors that also improve the quality of life.

In this novel proof-of-concept study, we presented the difference between reality and virtual reality based training in our first state-of-the-art, active seated posture training device, TruST. We also compared our results to a control group to identify the benefits of the assist-as-needed force strategy towards increasing seated postural range of motion. We defined postural stability as the ability to displace the estimated COM of the lower trunk segment further from the neutral postural configuration of reference without postural collapse of the upper body. The results demonstrate that both virtual reality and physical reality-based trainings, with assistive forces at and beyond the point of stability failure, enhance volitional control of seated trunk displacements. These outcomes follow motor learning theories where a challenging task oriented training can recruit and release the DOF to organize postural kinematics. In addition, we highlight the trade-off between reality and virtual reality training, where VR training could be performed more readily, be cost effective, be more cognitively engaging due to its game like nature, and provide variability in training at ease and in a low-cost environment, while physical training requires custom hardware and personnel for training. In future studies, we plan to investigate the changes in seated postural kinematics during game based variable tasks and the effect of VR posture training with TruST in patient populations.

It will be appreciated that the modules, processes, systems, and sections described above can be implemented in hardware, hardware programmed by software, software instruction stored on a non-transitory computer readable medium or a combination of the above. For example, a method for controlling a physical therapy system can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of control systems, robotics, and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, therapy and training methods, devices, and system. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A training/diagnostic machine, comprising
a fixed frame with servo-motor driven winches controlled by a controller, the winches having respective cables;
the frame surrounding a seating platform shaped and sized to accommodate the seat of a subject while in a seated position;
a body interface connected to the cables of the winches, the body interface being shaped and sized to engages the trunk of a subject seated in said seating platform such that the winches can apply forces to the trunk;
the controller being programmed to apply forces to the body interface to implement a therapeutic training program.

2. The machine of claim 1, wherein the body interface includes a donut-shaped harness that wraps around the trunk of a subject above the waist.

3. The machine of claim 1, wherein the controller is programmed to generate a force tunnel.

4. The machine of claim 1, wherein the cables have serially-connected force sensors and the forces are responsive to forces output by the force sensors.

5. The machine of claim 1, further comprising a virtual reality headset connected to the controller.

6. The machine of claim 5, wherein the controller is programmed to generate a virtual game that calls for a subject engaged in the body interface to interact with a virtual environment to cause the subject to lean in multiple directions in a seated position.

7. The machine of claim 5, wherein the controller is programmed to generate a virtual game that calls for a subject engaged in the body interface to interact with a virtual environment to cause the subject to reach for virtual objects with an extended arm from a seated position.

8. The machine of claim 1, wherein the controller is programmed to generate resistive forces in a first predefined range of motion of a subject and assistive forces in a second predefined range of motion of a subject.

9. The machine of claim 8, wherein the controller implements a virtual reality game in which the subject controls an object by motions of a hand with an unsupported arm.

10. The machine of claim 1, wherein the machine is used for both detecting postural or stability-maintaining competence and rehabilitation.

11. A training machine, comprising
a fixed frame with servo-motor driven winches controlled by a controller, the winches having respective cables;
a seating platform affixed to the frame, the seating platform being shaped and sized to accommodate the seat and feet of a subject while in a seated position;
a body interface connected to the cables of the winches, the body interface being shaped and sized to engages the trunk of a subject seated in said seating platform such that the winches can apply forces to the trunk under control of the controller;
the controller being programmed to apply forces to the body interface to implement a therapeutic training program.

12. The machine of claim 11, wherein the body interface includes a donut-shaped harness that wraps around the trunk of a subject above the waist.

13. The machine of claim 11, wherein the controller is programmed to generate a force tunnel.

14. The machine of claim 11, wherein the cables have serially-connected force sensors and the forces are responsive to forces output by the force sensors.

15. The machine of claim 11, further comprising a virtual reality headset connected to the controller.

16. The machine of claim 15, wherein the controller is programmed to generate a virtual game that calls for a subject engaged in the body interface to interact with a virtual environment to cause the subject to lean in multiple directions in a seated position.

17. The machine of claim 15, wherein the controller is programmed to generate a virtual game that calls for a subject engaged in the body interface to interact with a virtual environment to cause the subject to reach for virtual objects with an extended arm from a seated position.

18. A method for improving stabilization competence of a human subject, comprising:
seating the subject on a platform fixed in a frame having actuators;
connecting the actuators to the subject to apply pull and/or pushing forces to the subject;
using a posture detector including one of motion capture, accelerometers, optical image processing with machine classification of resulting processed images, and mechanical encoders, detecting that the subject is in a predefined postural position region, the region corresponding to one where the subject has been determined to have difficulty or inability to position or support his trunk and generating a signal indicating that the subject is in the predefined postural region; and
responsively to the signal, providing an increased level of support or assistance to facilitate movement or position control of the subject.

19. The method of claim 18, wherein the actuators include tension actuators.

20. The method of claim 18, wherein the actuators include linear actuators.

21. The method of claim 18, wherein the posture detector includes cameras at multiple locations, the controller processing images of the subject, or objects attached to the subject, to detect the subject position.

22. The method of claim 18, wherein the posture detector detects positions of markers.

23. A method of improving stabilization competence of a human subject, comprising:
positioning a support brace at a first predefined height above the hips on the trunk of a subject and providing dynamic assistance to the subject as he bends in various directions while recording a first boundary of a region of the subject's ability to control of the center of mass of the subject by detecting postural collapse;
positioning the support brace at a second predefined height above the hips on the trunk of a subject and providing dynamic assistance to the subject as he bends in various directions while recording a second boundary of a region of the subject's ability to control of the center of mass of the subject by detecting postural collapse;
identifying a position for the support brace for training the patient responsively to the first and second boundaries.

24. The method of claim 23, further comprising defining a first force field, using a controller, and applying the force field to actuators to provide assist-as-needed support while the subject moves through a prescribed series of positions to implement a training regimen.

25. The method of claim 24, further comprising, reassessing the boundary region after implementing said training regimen and defining a second force field, using the controller, and applying the force field to actuators to provide assist-as-needed support while the subject moves through a prescribed series of positions to implement a training regimen.

26. Apparatus for rehabilitation, comprising:
a controller connected to motorized actuators that are in turn connected to a brace attachable to a subject to provide posture support;
the controller generating a virtual reality representation of a challenge task that is performed by moving the brace in a manner that occurs when a subject wears the brace and changes his posture;
the controller providing assist-as-needed forces through the actuators to the brace according to prescribed boundary region for one or more predefined subjects.

27. The apparatus of claim 26, further comprising a seat adapted for a subject to sit upon.

28. The apparatus of claim 27, wherein the seat has force sensors and the controller is able to detect loss of posture control of a subject seated thereon while the subject performs virtual reality tasks.

* * * * *